(12) United States Patent
Woehr et al.

(10) Patent No.: US 8,057,431 B2
(45) Date of Patent: Nov. 15, 2011

(54) HINGED CAP FOR NEEDLE DEVICE

(75) Inventors: Kevin Woehr, Felsberg (DE); Hermann Riesenberger, Bebra (DE); Vince Leskowich, Karpathos (GR); Harald Heckmann, Lohfelden (DE); Michael Rubik, Morschen (DE)

(73) Assignee: B. Braun Melsungen AG, Melsungen (DE)

( * ) Notice: Subject to any disclaimer, the term of this patent is extended or adjusted under 35 U.S.C. 154(b) by 426 days.

(21) Appl. No.: 11/962,078

(22) Filed: Dec. 20, 2007

(65) Prior Publication Data

US 2008/0306451 A1  Dec. 11, 2008

Related U.S. Application Data

(60) Provisional application No. 60/876,246, filed on Dec. 21, 2006.

(51) Int. Cl.
*A61M 5/00* (2006.01)
(52) U.S. Cl. ............... 604/110; 604/164.08; 604/192; 604/198; 604/199; 604/263
(58) Field of Classification Search .......... 604/110, 604/198, 263, 192, 164.08, 199
See application file for complete search history.

(56) References Cited

U.S. PATENT DOCUMENTS

| | | | |
|---|---|---|---|
| 3,658,061 A | 4/1972 | Hall | |
| 4,631,057 A | 12/1986 | Mitchell | |
| 4,639,250 A | 1/1987 | Rycroft | |
| 4,664,259 A | 5/1987 | Landi | |
| 4,666,435 A | 5/1987 | Braginetz | |
| 4,723,943 A | 2/1988 | Spencer | |
| 4,725,267 A | 2/1988 | Vaillancourt | |
| 4,747,837 A | 5/1988 | Hauck | |
| 4,775,369 A | 10/1988 | Schwartz | |
| 4,778,453 A | 10/1988 | Lopez | |
| 4,795,432 A | 1/1989 | Karczmer | |
| 4,804,371 A | 2/1989 | Vaillancourt | |
| 4,804,372 A | 2/1989 | Laico et al. | |
| 4,813,940 A | 3/1989 | Parry | |

(Continued)

OTHER PUBLICATIONS

International Search Report completed and mailed Apr. 14, 2008 from corresponding PCT Application No. PCT/US2007/026234, filed Dec. 21, 2007 (3 pages).

(Continued)

*Primary Examiner* — Bhisma Mehta
*Assistant Examiner* — Larry R Wilson
(74) *Attorney, Agent, or Firm* — Klein, O'Neill & Singh, LLP

(57) ABSTRACT

A hinged cap device for use with a syringe includes a base defining an interior cavity for mounting onto a tip and a cap connected to the base by a living hinge. The cap is moveable from a ready position to an open position to expose a needle, and from the open position to a secured position to prevent relative rotation between the cap and the base. A first latching mechanism is on the cap for engaging the needle, the first latching mechanism locatable on a first side of the needle in the ready position and locatable on a second side of the needle in the secured position. The needle is disengageable from the first latching mechanism in the ready position, and the needle is not disengageable from the first latching mechanism in the secured position. The hinged cap device may also include a second latching mechanism to further prevent relative rotation between the cap and the base.

22 Claims, 25 Drawing Sheets

U.S. PATENT DOCUMENTS

| | | | |
|---|---|---|---|
| 4,816,024 A | 3/1989 | Sitar et al. | |
| 4,820,277 A | 4/1989 | Norelli | |
| 4,826,490 A | 5/1989 | Byrne et al. | |
| 4,832,696 A | 5/1989 | Luther et al. | |
| 4,846,809 A | 7/1989 | Sims | |
| 4,850,961 A | 7/1989 | Wanderer et al. | |
| 4,850,968 A | 7/1989 | Romano | |
| 4,850,977 A | 7/1989 | Bayless | |
| 4,850,994 A | 7/1989 | Zerbst et al. | |
| 4,850,996 A | 7/1989 | Cree | |
| 4,863,434 A | 9/1989 | Bayless | |
| 4,863,435 A | 9/1989 | Sturman et al. | |
| 4,867,746 A | 9/1989 | Durfresne | |
| 4,887,998 A | 12/1989 | Martin et al. | |
| 4,888,002 A | 12/1989 | Braginetz et al. | |
| 4,892,521 A | 1/1990 | Laico et al. | |
| 4,894,055 A | 1/1990 | Sudnak | |
| 4,900,311 A | 2/1990 | Stern et al. | |
| 4,909,792 A | 3/1990 | Norelli | |
| 4,911,706 A | 3/1990 | Levitt | |
| 4,917,673 A | 4/1990 | Coplin | |
| 4,921,490 A | 5/1990 | Spier et al. | |
| 4,923,446 A | 5/1990 | Page et al. | |
| 4,927,416 A | 5/1990 | Tomkiel | |
| 4,927,417 A | 5/1990 | Moncada et al. | |
| 4,929,237 A | 5/1990 | Medway | |
| 4,929,241 A | 5/1990 | Kulli | |
| 4,931,048 A | 6/1990 | Lopez | |
| 4,932,940 A | 6/1990 | Walker et al. | |
| 4,935,013 A | 6/1990 | Haber et al. | |
| 4,943,282 A | 7/1990 | Page et al. | |
| 4,944,731 A | 7/1990 | Cole | |
| 4,950,250 A | 8/1990 | Haber et al. | |
| 4,952,207 A | 8/1990 | Lemieux | |
| 4,955,866 A | 9/1990 | Corey | |
| 4,964,866 A | 10/1990 | Szware | |
| 4,976,699 A | 12/1990 | Gold | |
| 4,978,344 A | 12/1990 | Dombrowski et al. | |
| 4,982,842 A | 1/1991 | Hollister | |
| 4,985,021 A | 1/1991 | Straw et al. | |
| 5,000,740 A | 3/1991 | Ducharme et al. | |
| 5,015,240 A | 5/1991 | Soproni et al. | |
| 5,019,044 A | 5/1991 | Tsao | |
| 5,026,356 A | 6/1991 | Smith | |
| 5,049,136 A | 9/1991 | Johnson | |
| 5,053,017 A | 10/1991 | Chamuel | |
| 5,053,018 A | 10/1991 | Talonn et al. | |
| 5,057,089 A | 10/1991 | Greco | |
| 5,059,180 A | 10/1991 | McLees | |
| 5,084,030 A | 1/1992 | Byrne et al. | |
| 5,085,648 A | 2/1992 | Purdy et al. | |
| 5,092,851 A | 3/1992 | Ragner | |
| 5,104,384 A | 4/1992 | Parry | |
| 5,106,379 A | 4/1992 | Leap | |
| 5,106,380 A | 4/1992 | Lobello | |
| 5,116,326 A | 5/1992 | Schmidt | |
| 5,120,310 A | 6/1992 | Shaw | |
| 5,135,504 A | 8/1992 | McLees | |
| 5,139,489 A | 8/1992 | Hollister | |
| 5,141,500 A | 8/1992 | Hake | |
| 5,147,326 A | 9/1992 | Talonn et al. | |
| 5,151,088 A | 9/1992 | Allison et al. | |
| 5,151,089 A * | 9/1992 | Kirk et al. | 604/192 |
| 5,154,285 A | 10/1992 | Hollister | |
| 5,156,599 A | 10/1992 | Ranford et al. | |
| 5,160,326 A | 11/1992 | Talonn et al. | |
| 5,163,916 A | 11/1992 | Sunderland | |
| 5,163,918 A | 11/1992 | Righi et al. | |
| 5,169,392 A | 12/1992 | Ranford et al. | |
| 5,181,524 A | 1/1993 | Wanderer et al. | |
| 5,183,468 A | 2/1993 | McLees | |
| 5,188,611 A | 2/1993 | Orgain | |
| 5,188,613 A | 2/1993 | Shaw | |
| 5,201,708 A | 4/1993 | Martin | |
| 5,215,528 A | 6/1993 | Purdy et al. | |
| 5,217,437 A | 6/1993 | Talonn et al. | |
| 5,219,338 A | 6/1993 | Haworth | |
| 5,224,936 A | 7/1993 | Gallagher | |
| 5,232,454 A * | 8/1993 | Hollister | 604/192 |
| 5,232,455 A | 8/1993 | Hollister | |
| 5,242,416 A | 9/1993 | Hutson | |
| 5,242,417 A | 9/1993 | Paudler | |
| 5,242,418 A | 9/1993 | Weistein | |
| 5,246,427 A | 9/1993 | Sturman et al. | |
| 5,246,428 A | 9/1993 | Falknor | |
| 5,250,031 A | 10/1993 | Kaplan et al. | |
| 5,254,100 A | 10/1993 | Huband | |
| 5,256,151 A | 10/1993 | Chul | |
| 5,261,894 A | 11/1993 | Smith et al. | |
| 5,273,541 A | 12/1993 | Malenchek | |
| 5,273,543 A | 12/1993 | Bell et al. | |
| 5,277,311 A | 1/1994 | Hollister | |
| 5,290,254 A | 3/1994 | Vaillancourt | |
| 5,290,256 A | 3/1994 | Weatherford et al. | |
| 5,292,314 A | 3/1994 | D'Alession et al. | |
| 5,295,963 A | 3/1994 | Deeks | |
| 5,295,975 A | 3/1994 | Lockwood, Jr. | |
| 5,300,040 A | 4/1994 | Martin | |
| 5,300,045 A | 4/1994 | Plassche, Jr. | |
| 5,304,151 A | 4/1994 | Kuracina | |
| 5,312,368 A | 5/1994 | Haynes | |
| 5,312,369 A | 5/1994 | Arcusin et al. | |
| 5,314,414 A | 5/1994 | Hake et al. | |
| 5,318,547 A | 6/1994 | Altshuler | |
| 5,334,149 A | 8/1994 | Nortman et al. | |
| 5,334,158 A | 8/1994 | McLees | |
| 5,336,187 A | 8/1994 | Terry et al. | |
| 5,338,303 A | 8/1994 | King et al. | |
| 5,338,310 A | 8/1994 | Lewandowski | |
| 5,360,408 A | 11/1994 | Vaillancourt | |
| 5,364,370 A | 11/1994 | Szerlip et al. | |
| 5,366,447 A | 11/1994 | Gurley | |
| 5,368,568 A | 11/1994 | Pitts et al. | |
| 5,370,628 A | 12/1994 | Allison et al. | |
| 5,376,073 A | 12/1994 | Graves et al. | |
| 5,376,080 A | 12/1994 | Petrussa | |
| 5,385,551 A | 1/1995 | Shaw | |
| 5,389,076 A | 2/1995 | Shaw | |
| 5,395,347 A | 3/1995 | Blecher et al. | |
| 5,405,332 A * | 4/1995 | Opalek | 604/192 |
| 5,411,487 A | 5/1995 | Castagna | |
| 5,415,645 A | 5/1995 | Friend et al. | |
| 5,419,766 A | 5/1995 | Chang et al. | |
| 5,423,758 A | 6/1995 | Shaw | |
| 5,423,765 A | 6/1995 | Hollister | |
| 5,423,766 A | 6/1995 | Di Ceasare | |
| 5,425,720 A | 6/1995 | Rogalsky et al. | |
| 5,433,711 A | 7/1995 | Balaban et al. | |
| 5,433,712 A | 7/1995 | Stiles et al. | |
| 5,447,501 A | 9/1995 | Karlsson et al. | |
| 5,460,611 A | 10/1995 | Alexander | |
| 5,466,223 A | 11/1995 | Bressler et al. | |
| 5,472,430 A | 12/1995 | Vaillancourt et al. | |
| 5,478,313 A | 12/1995 | White | |
| 5,486,163 A | 1/1996 | Haynes | |
| 5,487,733 A | 1/1996 | Caizza et al. | |
| 5,489,272 A | 2/1996 | Wirtz | |
| 5,490,841 A | 2/1996 | Landis | |
| 5,498,243 A | 3/1996 | Vallelunga et al. | |
| 5,512,050 A | 4/1996 | Caizza et al. | |
| 5,527,294 A | 6/1996 | Weatherford et al. | |
| 5,533,974 A | 7/1996 | Gaba | |
| 5,536,257 A | 7/1996 | Byrne et al. | |
| 5,540,666 A | 7/1996 | Barta et al. | |
| 5,549,558 A | 8/1996 | Martin | |
| 5,549,570 A | 8/1996 | Rogalsky | |
| 5,549,572 A | 8/1996 | Byrne et al. | |
| 5,554,130 A | 9/1996 | McDonald et al. | |
| 5,554,131 A | 9/1996 | Lacivita | |
| 5,558,651 A | 9/1996 | Crawford et al. | |
| 5,562,624 A | 10/1996 | Righi et al. | |
| 5,562,626 A | 10/1996 | Sanpietro | |
| 5,573,512 A | 11/1996 | Van Den Haak | |
| 5,573,513 A | 11/1996 | Wozencroft | |
| 5,584,809 A | 12/1996 | Gaba | |
| 5,584,818 A | 12/1996 | Morrison | |
| 5,591,138 A | 1/1997 | Vaillancourt | |

| Patent | Date | Name |
|---|---|---|
| 5,595,566 A | 1/1997 | Vallelunga et al. |
| 5,599,310 A | 2/1997 | Bogert |
| 5,599,318 A | 2/1997 | Sweeney et al. |
| 5,601,535 A | 2/1997 | Byrne et al. |
| 5,601,536 A | 2/1997 | Crawford et al. |
| 5,603,699 A | 2/1997 | Shine |
| 5,630,803 A | 5/1997 | Tamaro |
| 5,632,733 A | 5/1997 | Shaw |
| 5,649,622 A | 7/1997 | Hollister |
| 5,662,610 A | 9/1997 | Sircom |
| 5,669,888 A | 9/1997 | Trapp |
| 5,683,365 A | 11/1997 | Brown et al. |
| 5,685,860 A | 11/1997 | Chang et al. |
| 5,695,474 A | 12/1997 | Daugherty |
| 5,695,476 A | 12/1997 | Harris |
| 5,697,907 A | 12/1997 | Gaba |
| 5,702,369 A | 12/1997 | Mercereau |
| 5,718,239 A | 2/1998 | Newby et al. |
| 5,720,727 A | 2/1998 | Alexander et al. |
| 5,733,264 A | 3/1998 | Flowers |
| 5,733,265 A | 3/1998 | Bachman et al. |
| 5,735,827 A | 4/1998 | Adwers et al. |
| 5,738,665 A | 4/1998 | Caizza et al. |
| 5,746,718 A | 5/1998 | Steyn |
| 5,746,726 A * | 5/1998 | Sweeney et al. ............... 604/263 |
| 5,746,727 A | 5/1998 | Graves et al. |
| 5,749,856 A | 5/1998 | Zadini et al. |
| 5,762,628 A | 6/1998 | Harper et al. |
| 5,769,827 A | 6/1998 | Demichelle et al. |
| 5,772,636 A | 6/1998 | Brimhall et al. |
| 5,776,107 A | 7/1998 | Cherif-Cheikh |
| 5,779,684 A | 7/1998 | Tamaro |
| 5,792,121 A | 8/1998 | Tamaro |
| 5,792,122 A | 8/1998 | Brimhall et al. |
| 5,795,336 A | 8/1998 | Romano et al. |
| 5,795,339 A | 8/1998 | Erskine |
| 5,807,351 A | 9/1998 | Kashmer |
| 5,807,352 A | 9/1998 | Tamaro |
| 5,810,784 A | 9/1998 | Tamaro |
| 5,814,017 A | 9/1998 | Kashmer |
| 5,817,064 A | 10/1998 | Demarco et al. |
| 5,817,070 A | 10/1998 | Tamaro |
| 5,820,605 A | 10/1998 | Zdeb et al. |
| 5,823,997 A | 10/1998 | Thorne |
| 5,836,920 A | 11/1998 | Robertson |
| 5,843,041 A | 12/1998 | Hake et al. |
| 5,853,393 A | 12/1998 | Bogert |
| 5,868,716 A | 2/1999 | Sweeney et al. |
| 5,879,337 A | 3/1999 | Kuracina et al. |
| 5,893,845 A | 4/1999 | Newby et al. |
| 5,894,015 A | 4/1999 | Rechtin |
| 5,899,883 A | 5/1999 | Chern et al. |
| 5,910,130 A | 6/1999 | Caizza et al. |
| 5,919,168 A | 7/1999 | Wheeler |
| 5,947,936 A | 9/1999 | Bonds |
| RE36,398 E | 11/1999 | Byrne et al. |
| 5,976,111 A | 11/1999 | Hart |
| 5,980,488 A | 11/1999 | Thorne |
| 5,980,494 A | 11/1999 | Malenchek et al. |
| 5,984,899 A | 11/1999 | D'Alessio et al. |
| RE36,447 E | 12/1999 | Byrne et al. |
| 6,001,080 A | 12/1999 | Kuracina et al. |
| 6,004,294 A | 12/1999 | Brimhall et al. |
| 6,010,487 A | 1/2000 | Demichele et al. |
| 6,013,059 A | 1/2000 | Jacobs |
| 6,015,396 A | 1/2000 | Buttgen et al. |
| 6,017,329 A | 1/2000 | Hake |
| 6,056,726 A | 5/2000 | Isaacson |
| 6,077,253 A | 6/2000 | Cosme |
| 6,080,135 A | 6/2000 | Van Stokkum |
| 6,090,079 A | 7/2000 | Fu |
| 6,099,504 A | 8/2000 | Gross et al. |
| 6,102,920 A | 8/2000 | Sullivan et al. |
| 6,117,110 A | 9/2000 | Radmand |
| 6,120,482 A | 9/2000 | Szabo |
| 6,129,710 A | 10/2000 | Padgett et al. |
| 6,132,401 A | 10/2000 | Van Der Meyden et al. |
| 6,149,630 A | 11/2000 | Robinson |
| 6,159,185 A | 12/2000 | Tanihata |
| 6,165,153 A | 12/2000 | Kashmer |
| 6,171,283 B1 | 1/2001 | Perez et al. |
| 6,171,284 B1 | 1/2001 | Kao et al. |
| 6,183,445 B1 | 2/2001 | Lund et al. |
| 6,183,446 B1 | 2/2001 | Jeanbourquin |
| 6,186,980 B1 | 2/2001 | Brunel |
| 6,190,361 B1 | 2/2001 | Gettig et al. |
| RE37,110 E | 3/2001 | Hollister |
| 6,203,527 B1 | 3/2001 | Zadini et al. |
| 6,206,853 B1 | 3/2001 | Bonnet |
| 6,210,373 B1 | 4/2001 | Allmon |
| 6,213,983 B1 | 4/2001 | Cherif-Cheikh |
| 6,213,987 B1 | 4/2001 | Hirsch et al. |
| 6,217,559 B1 | 4/2001 | Foster |
| RE37,252 E | 7/2001 | Hollister |
| 6,254,575 B1 | 7/2001 | Thorne, Jr. et al. |
| 6,261,264 B1 | 7/2001 | Tamaro |
| 6,261,265 B1 | 7/2001 | Mosseri |
| 6,273,874 B1 | 8/2001 | Parris |
| 6,277,102 B1 | 8/2001 | Carilli |
| 6,280,420 B1 | 8/2001 | Ferguson |
| 6,287,278 B1 | 9/2001 | Woehr et al. |
| 6,298,541 B1 | 10/2001 | Newby et al. |
| 6,299,602 B1 | 10/2001 | Miller et al. |
| 6,302,868 B1 | 10/2001 | Mohammad |
| 6,309,376 B1 | 10/2001 | Alesi |
| 6,319,232 B1 | 11/2001 | Kashmer |
| 6,319,233 B1 | 11/2001 | Jansen et al. |
| 6,319,234 B1 | 11/2001 | Restelli et al. |
| 6,322,540 B1 | 11/2001 | Grabis et al. |
| 6,328,713 B1 | 12/2001 | Hollister |
| 6,344,032 B1 | 2/2002 | Perez et al. |
| 6,355,021 B1 | 3/2002 | Nielsen et al. |
| 6,409,705 B1 | 6/2002 | Kondo |
| 6,409,706 B1 | 6/2002 | Loy |
| 6,413,243 B1 | 7/2002 | Geist |
| 6,416,323 B1 | 7/2002 | Grenfell et al. |
| 6,425,884 B1 | 7/2002 | Wemmert et al. |
| 6,436,086 B1 | 8/2002 | Newby et al. |
| 6,440,104 B1 | 8/2002 | Newby et al. |
| 6,443,929 B1 | 9/2002 | Kuracina et al. |
| 6,475,190 B2 | 11/2002 | Young |
| 6,475,191 B2 | 11/2002 | Tamura et al. |
| 6,475,194 B2 | 11/2002 | Domici, Jr. et al. |
| 6,485,469 B1 | 11/2002 | Stewart et al. |
| 6,511,460 B1 | 1/2003 | Arnissolle |
| 6,527,747 B2 | 3/2003 | Adams et al. |
| 6,537,257 B1 | 3/2003 | Wein |
| 6,537,259 B1 | 3/2003 | Niermann |
| 6,719,737 B2 | 4/2004 | Kobayashi |
| D505,200 S | 5/2005 | Simpson et al. |
| 6,951,551 B2 | 10/2005 | Hudon |
| 2003/0181860 A1 | 9/2003 | Swenson |
| 2003/0181868 A1 | 9/2003 | Swenson |
| 2005/0004531 A1 * | 1/2005 | Hwang et al. ............... 604/263 |
| 2006/0149188 A1 | 7/2006 | Simas, Jr. |

OTHER PUBLICATIONS

Written Opinion completed and mailed Apr. 14, 2008 from corresponding PCT Application No. PCT/US2007/026234, filed Dec. 21, 2007 (7 pages).

Preliminary Report mailed Jul. 2, 2009 from corresponding PCT Application No. PCT/US2007/026234, filed Dec. 21, 2007 (3 pages).

* cited by examiner

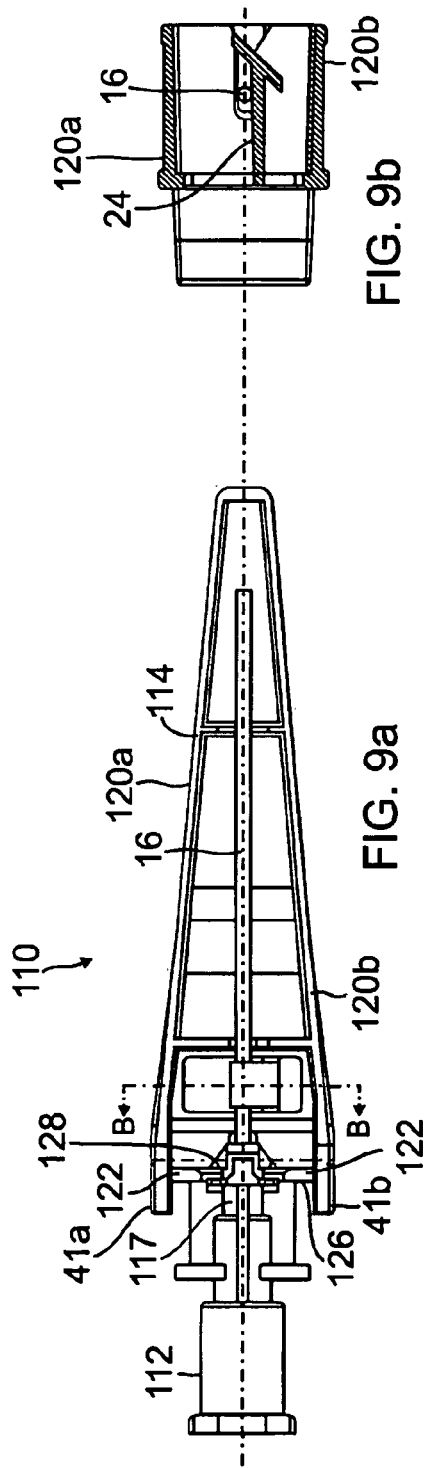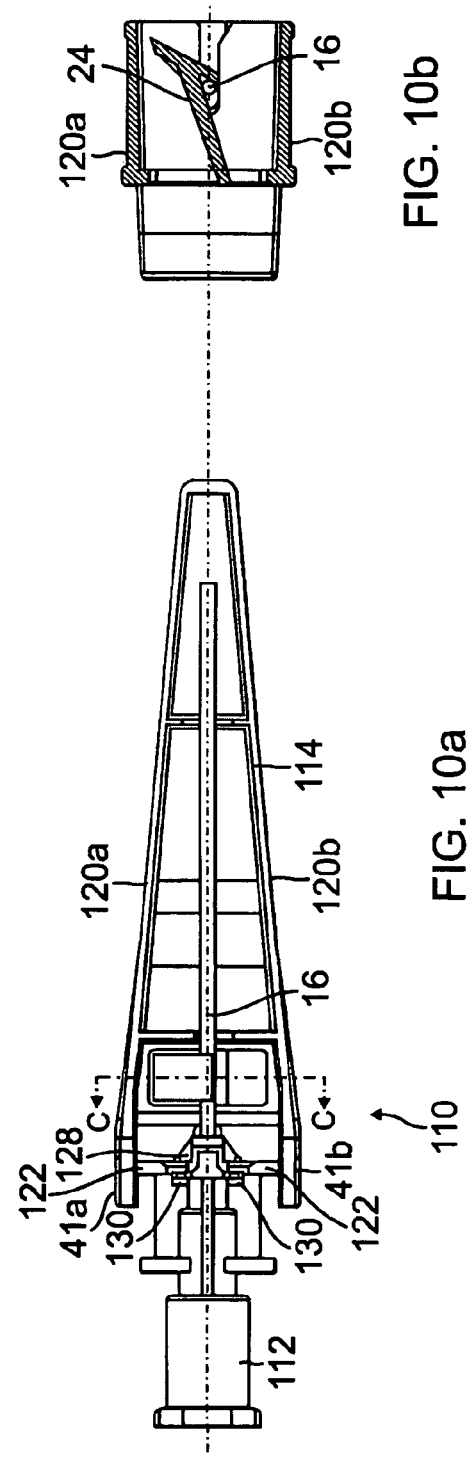

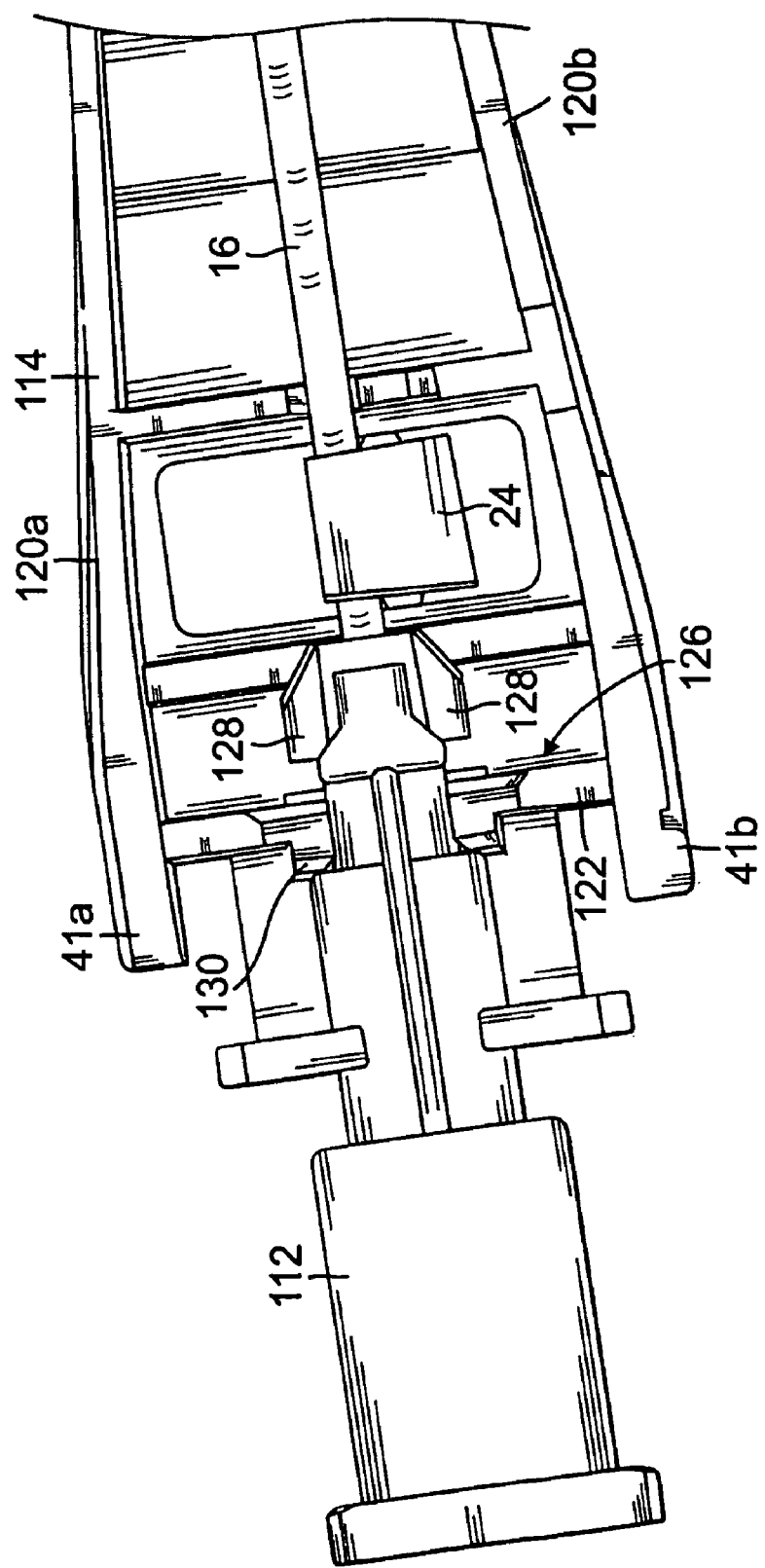

HINGED CAP FOR NEEDLE DEVICE

CROSS-REFERENCE TO RELATED APPLICATION(S)

This application claims priority to and the benefit of U.S. Provisional Application No. 60/876,246, filed on Dec. 21, 2006, in the United States Patent and Trademark Office, the entire contents of which are expressly incorporated herein by reference.

FIELD OF ART

The present invention relates generally to caps for a needle device, and more particularly, to hinged cap devices for use with hypodermic needles.

BACKGROUND

Recapping is a common procedure for periods between drawing up fluids into a syringe and administering injections through a needle. The recapping procedure can occasionally cause needle sticks since users sometime misalign the needles with the openings on the caps, producing minimal pain but causing a great deal of inconvenience because all such needle stick incidences must be reported. Also, since needles related to the needle stick incidences must be discarded, medications contained within the syringes are unnecessarily wasted. Furthermore, fluids linked to these "clean" type of needle sticks can cause injuries and adverse reactions. In an effort to reduce or eliminate the source of "clean" needle stick injuries during recapping between drawing up fluids and administering an injection, it was necessary to improve the state of the art. The improvements will also minimize or eliminate the more dangerous types of needle stick injuries that occur after the needles have been contaminated with a patient's bodily fluids. In exemplary embodiments discussed below, hinged cap devices are packaged ready for use without additional removable caps. However, in some cases, a removable cap may still be used as necessary or desired.

As further discussed below, using a hinged safety cap device having multiple positions will allow a user to safely cover a sharp needle tip during the periods between drawing up fluids and administering an injection to a patient. The needle can be covered without locking the device to allow the needle to be exposed when necessary. Before the user discards the device, such as after use, he or she can manipulate the hinged cap into a locked position so it can no longer be re-used or be exposed to cause needle stick injuries. In some exemplary embodiments, an audible, visual and/or tactile signal(s) is provided to the user as an indication that the cap is securely locked over the needle.

SUMMARY

A hinged cap device for use with a syringe includes a base defining an interior cavity for mounting onto a tip and a cap connected to the base by a living hinge. The cap is moveable from a ready position to an open position to expose a needle, and from the open position to a secured position to prevent relative rotation between the cap and the base. A first latching mechanism is on the cap for engaging the needle, the first latching mechanism locatable on a first side of the needle in the ready position and locatable on a second side of the needle in the secured position. The needle is disengageable from the first latching mechanism in the ready position, and the needle is not disengageable from the first latching mechanism in the secured position.

In certain aspects of the present invention, the hinged cap assembly may optionally include a first latching mechanism having a projection attached to the cap and extending into the open channel and a catch lever straddling the projection to form an obtuse angle side and an acute angle side.

The hinged cap device may also include a second latching mechanism on the cap for engaging at least one tab on the cap, the second latching mechanism dis-engageable from the at least one tab by axially moving the cap along a lengthwise axis of the needle relative to the hub. In certain aspects of the present invention, the second latching mechanism may optionally include a pair of latch walls, one latch wall extending from the first side wall and the second side wall, wherein each latch wall comprises a notch adapted to engage a respective base tab on the base.

In another exemplary embodiment, the second latching mechanism may include a pair of tabs, one tab extending from both the first side wall and the second side wall, wherein each tab is adapted to abut a respective base tab on the base.

In certain aspects of the present invention, the hinged cap assembly may further optionally include a base having a wedge and a cap having a pair of gripping plates, the wedge adapted to engage the gripping plates to temporarily maintain the cap in the open position. The hinged cap device may be a single integral device and the device may be injection molded. The hinged cap assembly may also optionally include a first side wall having a notch having two end wall edges defining an angle therebetween. Additionally, a living hinge may be located on the cap spaced from the living hinge located between the cap and the base.

Also provided is a method for operating a hinged cap device including moving a cap axially along a lengthwise direction of a needle to distort the living hinge to disengage the second latching mechanism from the base and rotating the cap radially outwardly relative to the needle from the ready position to the open position to expose the needle, and engaging the cap to the base in the cap open position. The method may also include rotating the cap radially inwardly relative to the needle to shield the needle from the open position to the secured position, thereby engaging the needle latching mechanism with the needle.

BRIEF DESCRIPTION OF THE DRAWINGS

FIG. 9a is a top view of the hinged cap device of FIG. 8 in a ready position, looking at the channel of the cap;

FIG. 9b is a cross-sectional view of the hinged cap device of FIG. 9a along the line B-B;

FIG. 9c is a side detail view of the hinged cap device of FIG. 8 with the base disengaged from the second latching mechanism;

FIG. 10a is a side view of the hinged cap device of FIG. 8 in a secured position, looking at the channel of the cap;

FIG. 10b is a cross-sectional view of the hinged cap device of FIG. 9a along the line C-C;

DETAILED DESCRIPTION

The detailed description set forth below in connection with the appended drawings is intended as a description of exemplary embodiments of a hinged cap assembly for use with needles having sharp needle tips provided in accordance with aspects of the present invention and is not intended to represent the only forms in which the present invention may be constructed or used. The description sets forth the features and the steps for constructing and using the hinged cap assembly of the present invention in connection with the illustrated embodiments. It is to be understood that the same or equivalent functions and structures may be accomplished by different embodiments and are also intended to be encompassed within the spirit and scope of the present invention, especially those incorporating a combination of features shown in the different embodiments included herein. As denoted elsewhere herein, like element numbers are intended to indicate like or similar elements or features.

Figure 1:
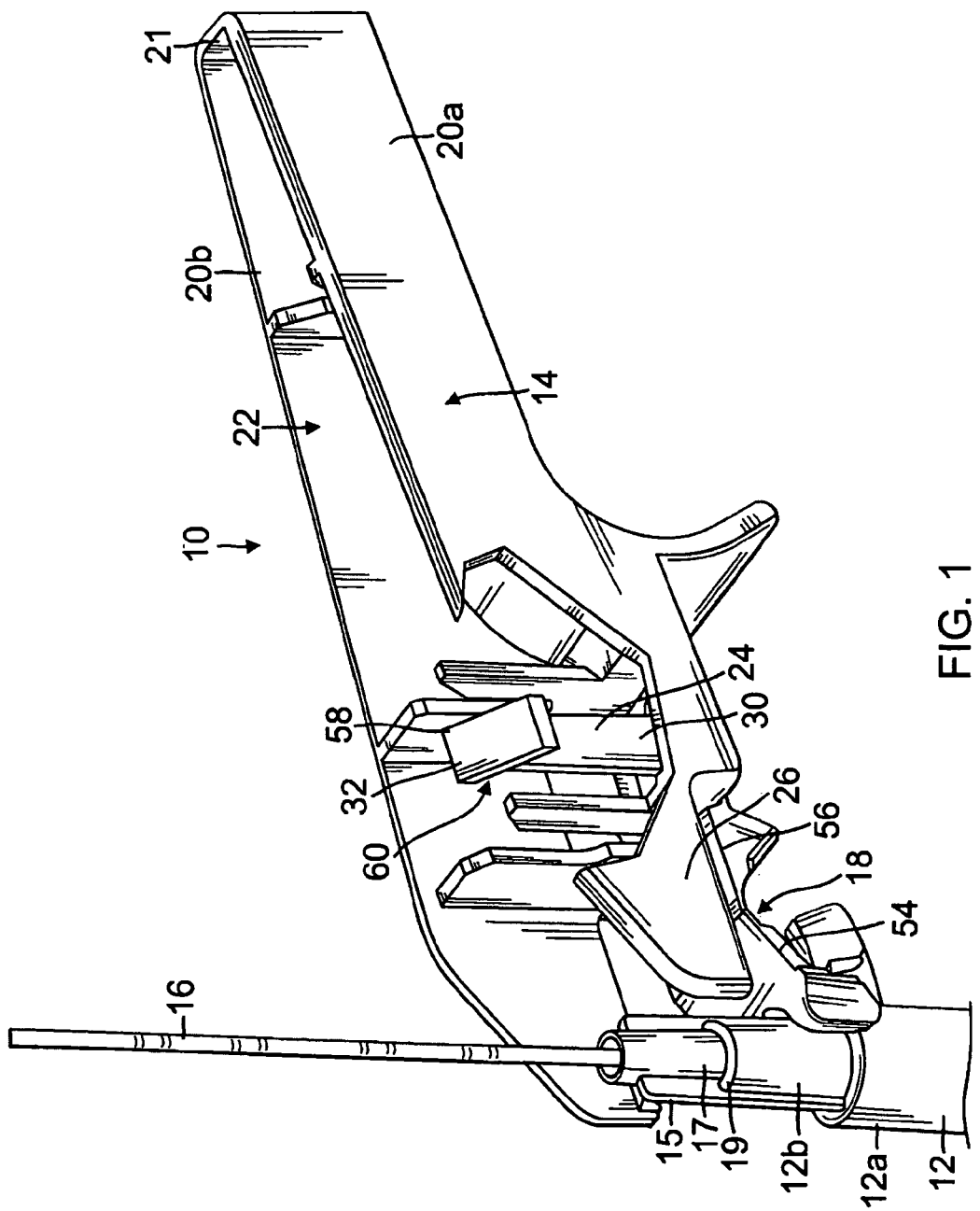
FIG. 1 is a perspective view of a hinged cap device provided in accordance with aspects of the present invention.
Figure 7:
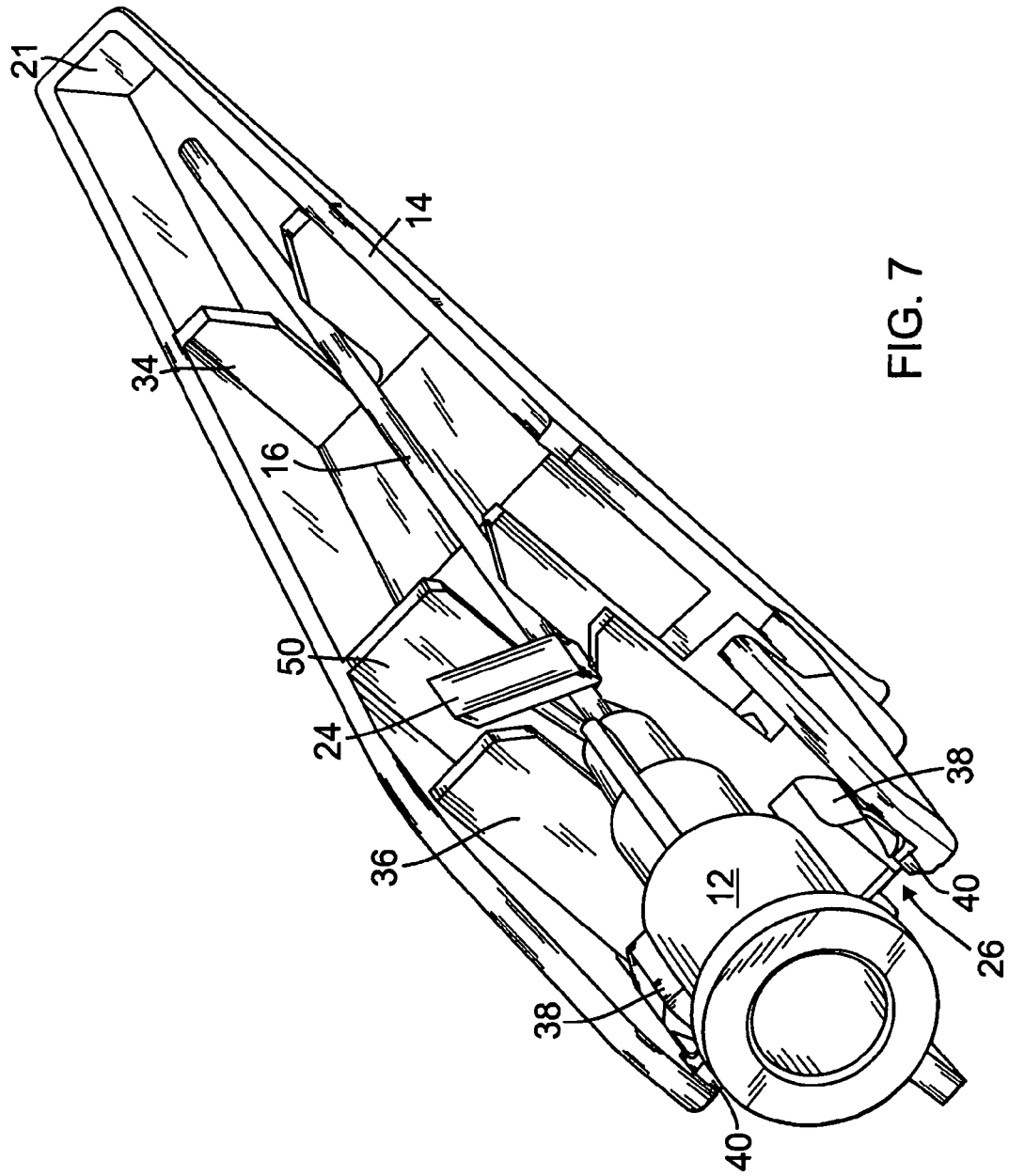
FIG. 7 is a perspective view of the hinged cap device of FIG. 1 in a secured configuration.
Figure 8:
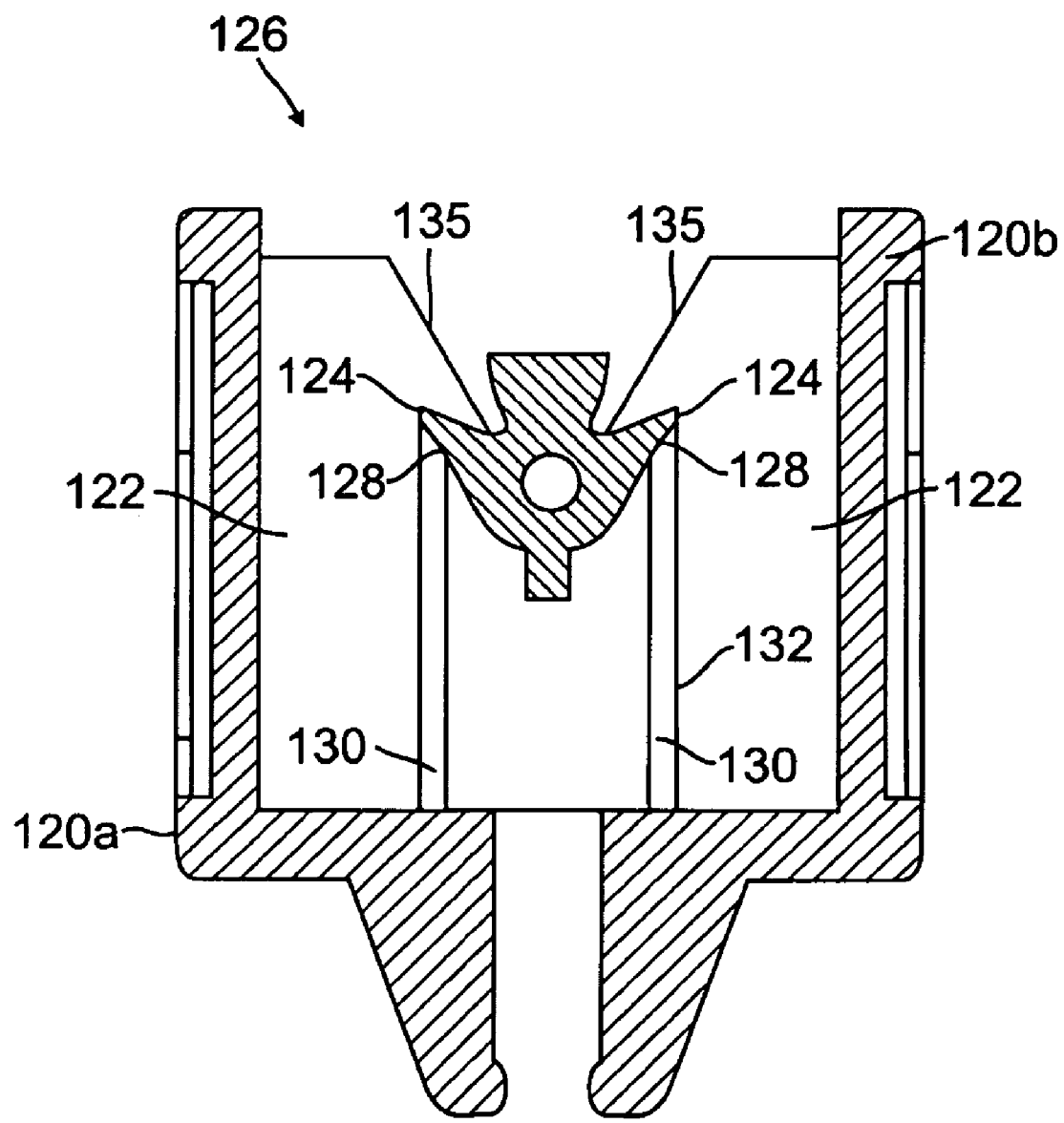
FIG. 8 is a cross-sectional detail view of a proximal end of a cap of another embodiment of the hinged cap device in accordance with aspects of the present invention showing a second latch mechanism.

Referring now to FIG. 1, a perspective view of an exemplary hinged cap assembly is shown, which is generally designated as 10. Broadly speaking, the hinged cap assembly 10 comprises a base or hub 12 for mounting onto a syringe tip (not shown), the base defining an interior cavity therein, and a cap 14 for shielding the needle 16 preceding or following an injection. The hinged cap assembly 10 may be made by injection molding and, in one exemplary embodiment, is an integrally formed single unit in which the base 12 is connected to the cap 14 by a living hinge 18. As will be described in more detail below, the cap 14 is rotatable with respect to the base 12 from a packaged or ready position (FIG. 2) to an open position (FIG. 1) and from the open position to a secured position (FIG. 7).

Figure 2:
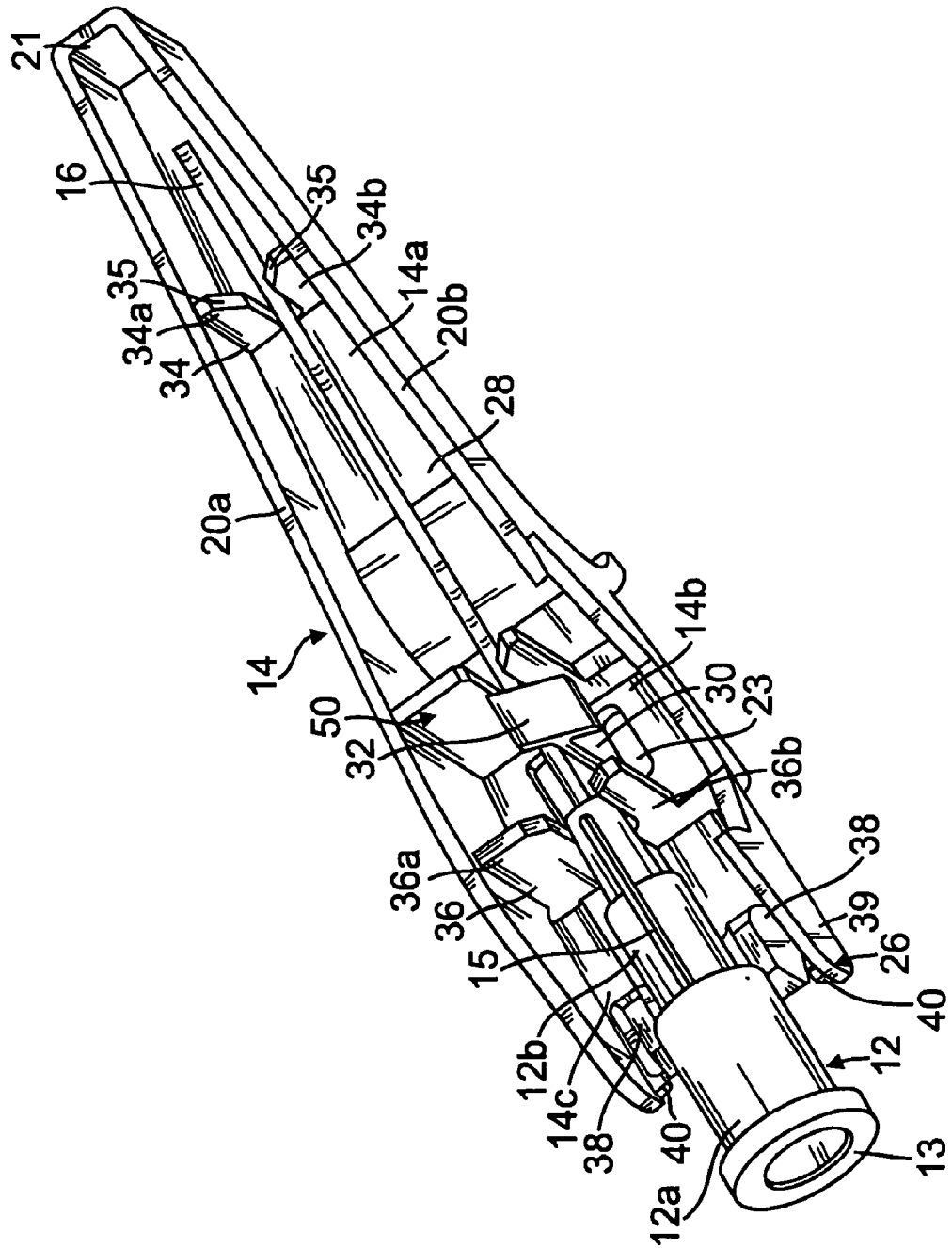
FIG. 2 is a perspective view of the hinged cap device of FIG. 1 showing the cap in a packaged or pre-operative configuration.

With reference now to FIGS. 1 and 2, in one exemplary embodiment, the base 12 includes two integral cylinders 12a, 12b with the second cylinder 12b having a smaller diameter than the first cylinder. The first cylinder 12a is dimensioned to receive a syringe tip (not shown) of a syringe. The syringe tip and the hub may engage one another using Luer tapers with the flange 13 located at a proximal end of the first cylinder 12a optionally engaging a threaded collar on the syringe to form a Luer lock, as is well known in the art. An integral coaxial cylindrical needle holder 17 extends distally from the base 12 for securing a needle 16 to the base. The needle holder 17 is dimensioned with a smaller diameter than the base and is adapted to be received by a hub alignment mechanism 36 when the hinged cap device 10 is in the ready position and in the secured position, as described in more detail below. A stopping edge 19 is formed by a distal surface of the second cylinder 19b to limit axial movement of the base 12 with respect to the cap 14, as described in more detail below. In an alternative embodiment, the base may incorporate a male projection for engaging a separate combination needle hub and needle. The alternative male projection (not shown) may be a male Luer taper having an optional Luer lock, which may be a collar having internal threads, as is well known in the art. Optionally, a ridge or rib 15 in incorporated on the second cylinder 12b and the needle holder 17 for reinforcement. IN the embodiment shown, two spaced apart ribs are incorporated, with only one shown.

The cap 14 generally is configured to shield and contain the needle 16 in the ready and secured positions to be easily manipulated between the ready and open positions; and to be easily manipulated between the open and secured positions. The cap 14 comprises a base wall 28 and two side walls 20a, 20b, defining a generally U-shaped or otherwise open channel 22 therebetween. As seen more clearly in FIG. 5, a profile of the cap 14 includes a middle section 14b that extends deeper than a distal section 14a and a proximal section 14c. The base wall 28 substantially follows the contour of the profile and serves to support various components of the cap, as described in more detail below. The side walls 20a, 20b extend upward from the base wall 28 and are generally parallel to each other in the proximal section 14c of the cap 14. In the middle and distal sections 14b, 14a, the side walls 20a, 20b are configured to form a narrowingly tapered distally extending channel. An end wall 21 extends between the two side walls 20a, 20b at a distal end of the cap 14. In alternative embodiments, the side walls 20a, 20b may extend generally parallel to one another along the entire length of the cap.

Figure 4:
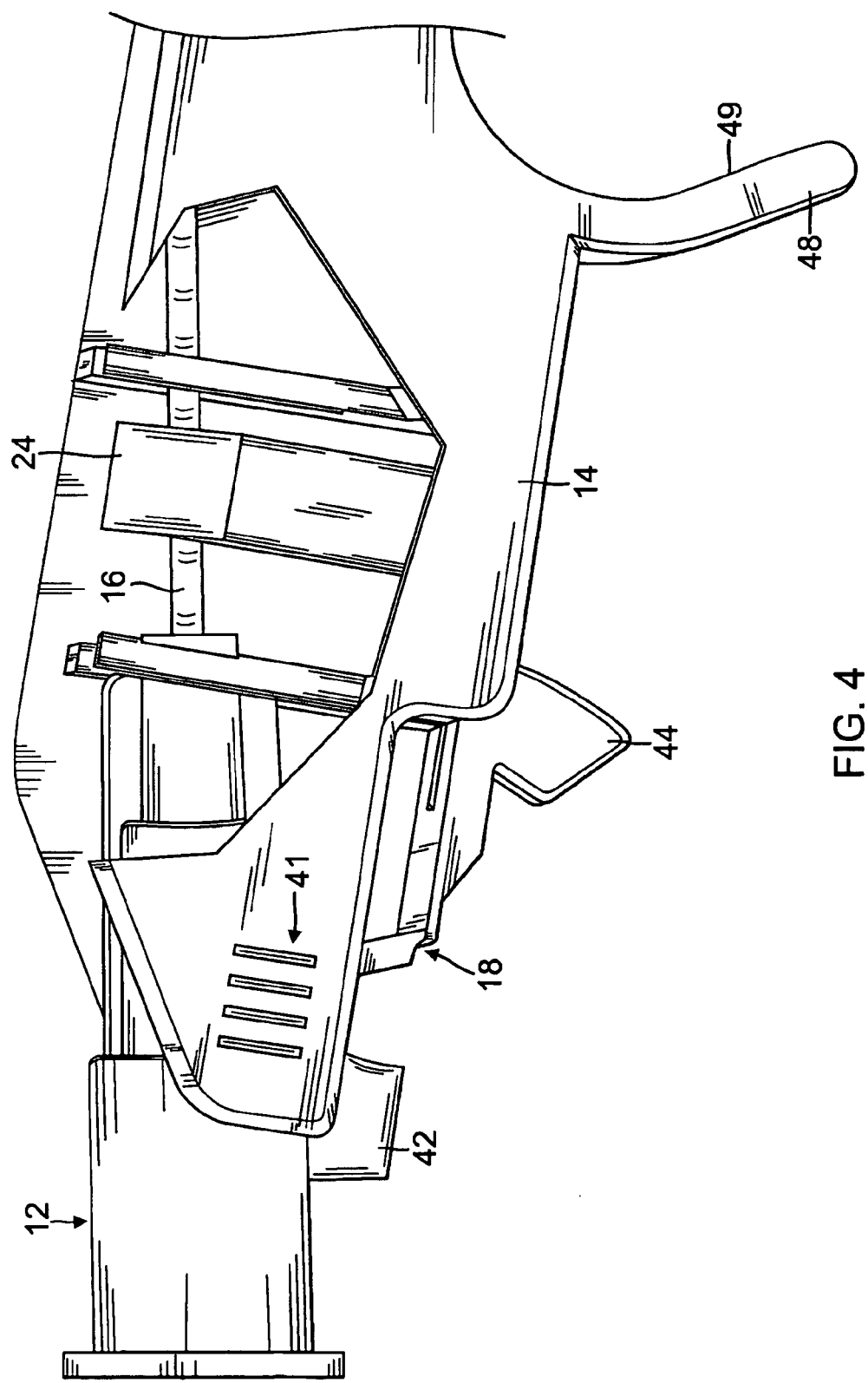
FIG. 4 is a side view of the hinged cap device of FIG. 3 showing a living hinge partially distorted for uncapping the needle.

As shown in the figures, such as FIGS. 1 and 4, a portion of the side wall 20a is cut away, for discussion purposes, to expose a first latching mechanism 24 provided in accordance with aspects of the present invention. The first latching mechanism 24 comprises a cantilever projection 30 extending generally orthogonally of the base wall and a sloped catch lever 32 integral with a top surface of the projection. In one exemplary embodiment, the projection 30 is attached to a circumferential surface of an opening 23 in the base wall 28 located in the middle portion 14b of the cap 14 and extends into the channel 22. Since only a lower portion of the projection 30 is attached to the opening, the projection has lateral flexibility with respect to a longitudinal axis of the needle 16. The sloped catch lever 32 straddles the projection 30, forming an obtuse angle with one side of the projection and an acute angle on the other side of the projection. The obtuse angle side of the sloped catch lever 32 has a configuration such that when a bottom surface 60 (FIG. 1) of the sloped catch lever encounters the needle 16 when the cap moves from a ready position to an open position, the first latch mechanism 24 is displaced and the catch lever can pass around the needle. Alternatively or in addition thereto, the needle 16 may deflect or bend slightly to pass around the obtuse angle side. The acute angle side of the sloped catch lever 32 has a configuration such that when a top surface 58 of the catch lever encounters the needle 16 when the cap moves from an open position to the secured position, the first latch mechanism 24 is displaced and/or the needle is deflected and the needle can then pass around the catch lever. However, if a user attempts to reposition the cap 14 into the open position from the secured position, and thereby pushes the bottom surface 60 of the acute angle side of the catch lever 32 against the needle, the needle cannot laterally displace the first latch mechanism 24 nor can the needle pass around the sloped catch lever, thereby maintaining the hinged cap device 10 in the secured position.

With reference again to FIG. 2, in one exemplary embodiment, the channel 22 incorporates a first needle alignment mechanism 34 for aligning the needle 16 to the cap 14, the first needle alignment mechanism being located within the distal section 14a of the cap. The first needle alignment mechanism 34 comprises a pair of aligned vertical walls 34a, 34b, one wall extending perpendicularly from each side wall 20a, 20b, having a gap therebetween adapted to receive the needle 16 and align it with a longitudinal axis of the cap 14. Each wall 34a, 34b of the first needle alignment mechanism 34 includes a sloped leading edge 35 for directing the needle 16 into the gap between the walls when the cap is rotated from an open position to a secured position. Similarly, the channel 22 may incorporate a second needle alignment mechanism 50 having substantially the same structure as the first needle alignment mechanism in the middle section 14b, for example, and located distally adjacent the first latching mechanism 24.

In another exemplary embodiment, a hub alignment mechanism 36 may be incorporated into the cap 14 for aligning the base 12 to the cap. Similarly to the first and second needle alignment mechanisms 34, 50, the hub alignment mechanism 36 includes two spaced walls 36a, 36b extending perpendicularly to side walls 20a, 20b, a forming a gap between each wall having a sloped leading edge 35. The gap between the walls 36a, 36b is dimensioned to receive the needle holder 17, and therefore is wider than the gap between walls of the first and second needle alignment mechanisms 34, 50, and is located proximal to the first catch mechanism.

Each sidewall 20a, 20b comprises an integral fin 39 extending proximally from about the hub alignment mechanism 36, the fins having a sloped top surface and a generally flat bottom surface. In one exemplary embodiment, the fins 39 includes an exterior indicia 41 (FIG. 4), which may be, for example, a series of slightly raised protrusions, a roughened or corrugated surface, or a contoured surface. The exterior indicia 41 adds to the aesthetic appeal of the cap. In other embodiments, the cap may include lettering, symbols, or instructions. Alternatively or in addition, exterior indicia 41 indicates to a user where to hold the cap 14 and also to allow the user to attain a more secure grip of the cap when moving the cap between the various positions. An integral ear, lever, or tab 40 extends into the channel 22, the tabs being generally located toward a lower, proximal portion of each fin 39. The tabs 40 are configured to abut corresponding tabs 38 extending from the base 12 to prevent relative movement between the cap 14 and the base in the ready position. More specifically, the tabs 38 extend from the second cylinder 12b and have a flat bottom surface adapted to abut a flat top surface of the tabs 40. The two sets of tabs provide a temporary lock state and function as an added security feature when in the ready position.

Figure 5:
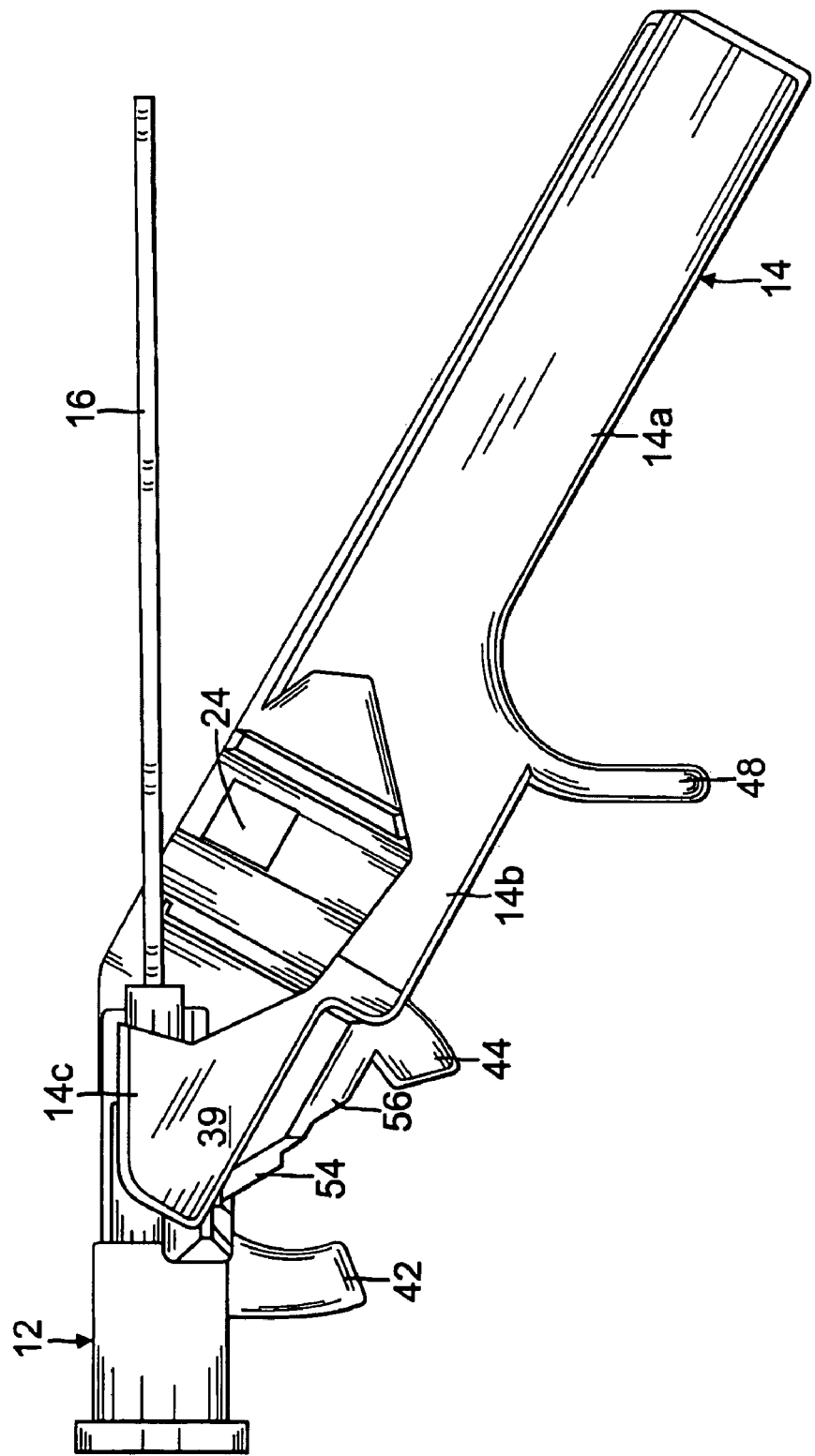
FIG. 5 is a side view of the hinged cap device of FIG. 1 showing the cap rotated away from the needle to expose the needle.

The base 12 is connected to the cap 14 by a living hinge 18 located between a base segment 54 and a cap segment 56. As shown in FIGS. 1 and 5, the cap segment 56 extends proximally from a proximal end of the base wall 28 and is generally parallel to a longitudinal axis of the cap 14. The base segment 54 extends at an angle from a wall surface of the base 12 towards the cap segment 56 with the living hinge 18 integrally joined therebetween such that the living hinge not only allows rotation of the cap 14 relative to the base 12, but also allows for limited axial movement of the cap relative to the base to enable the tabs 38, 40 to be disengaged, as is described in more detail below.

With reference now also to FIG. 4, the cap 14 comprises an integral push lever 48 extending from the base wall 28 away from the channel 22. In one exemplary embodiment, a distally-facing surface 49 of the push lever 48 is generally arc-shaped and dimensioned to generally conform to the side of a user's finger. As such, the user can use the push lever 48 to apply a compressive axial force toward a proximal end of the cap, and also apply a radial force to rotate the cap 14 with respect to the base 12. One of ordinary skill in the art will appreciate that other configurations of a push lever, such as an orthogonal lever, may be used within the spirit and scope of aspects of the present invention. Additionally, a user may simply grab the two side walls 20a, 20b to exert both an axial force and a radial force to open the cap. Still alternatively, a user can push the cap against a surface so that the end wall 21 of the cap (FIG. 2) abuts the surface to create an axial force and a rotational force to open the cap.

Figure 6:
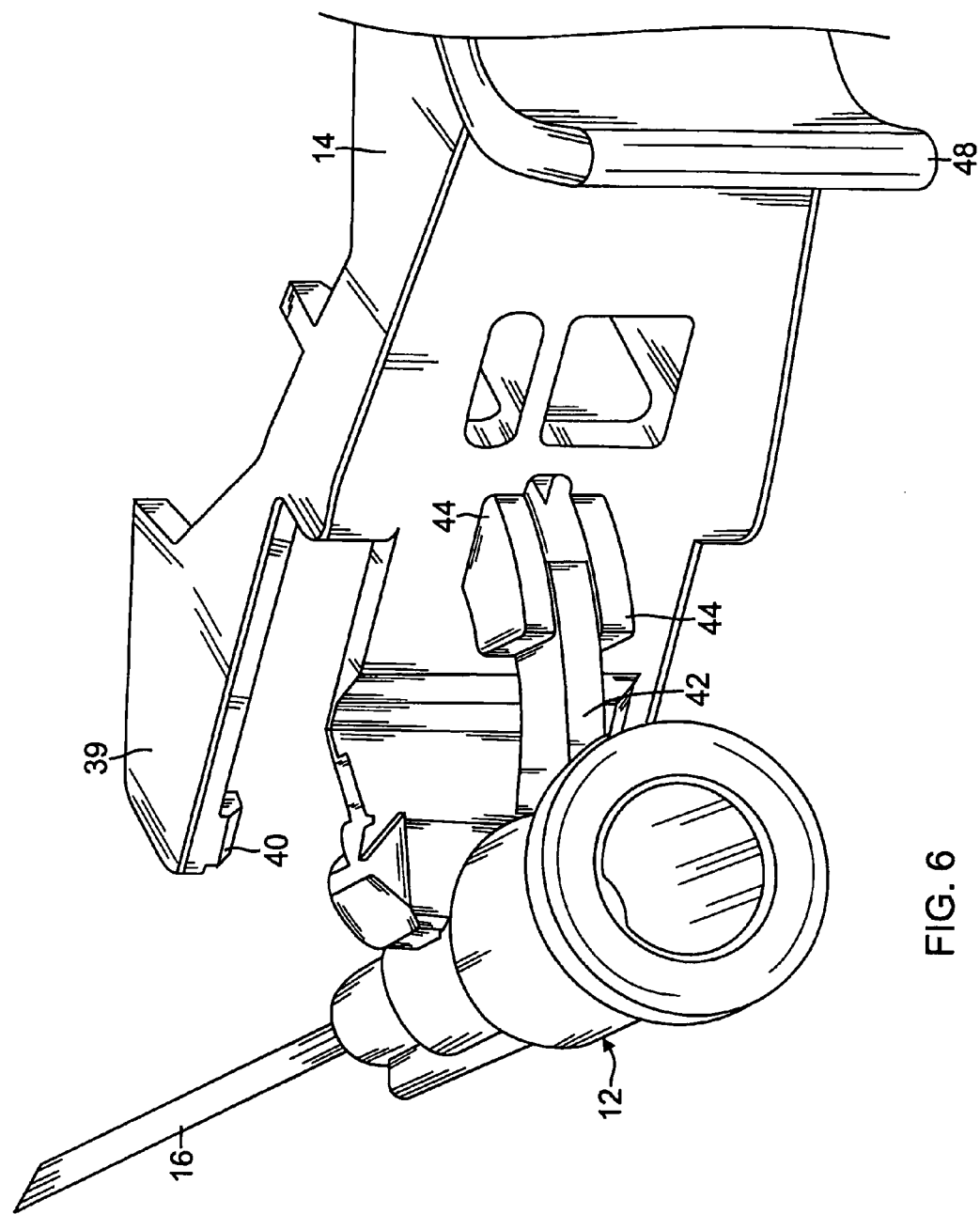
FIG. 6 is a perspective end view of the hinged cap device of FIG. 1 showing the cap rotated away from the needle to expose the needle.

With reference now to FIGS. 4-6, and initially to FIG. 6, a wedge 42 extends from a wall surface of the base 12, the wedge having a slightly arcuate configuration. The wedge 42 is dimensioned to fit between two spaced gripping plates 44 which extend from the base wall 28 of the cap 14 (FIG. 6). More specifically, the wedge 42 is located on the base 12 such that when the cap 14 is rotated by a certain amount about the living hinge 18 with respect to the base, the wedge engages the gripping plates 44 to temporarily retain the cap in the open position. In one exemplary embodiment, the engagement between the wedge 42 and the gripping plates 44 is a frictional engagement. However, one of ordinary skill in the art will appreciate that toothed surfaces or detents may be used without deviating from the spirit and scope of the present invention.

Figure 3:
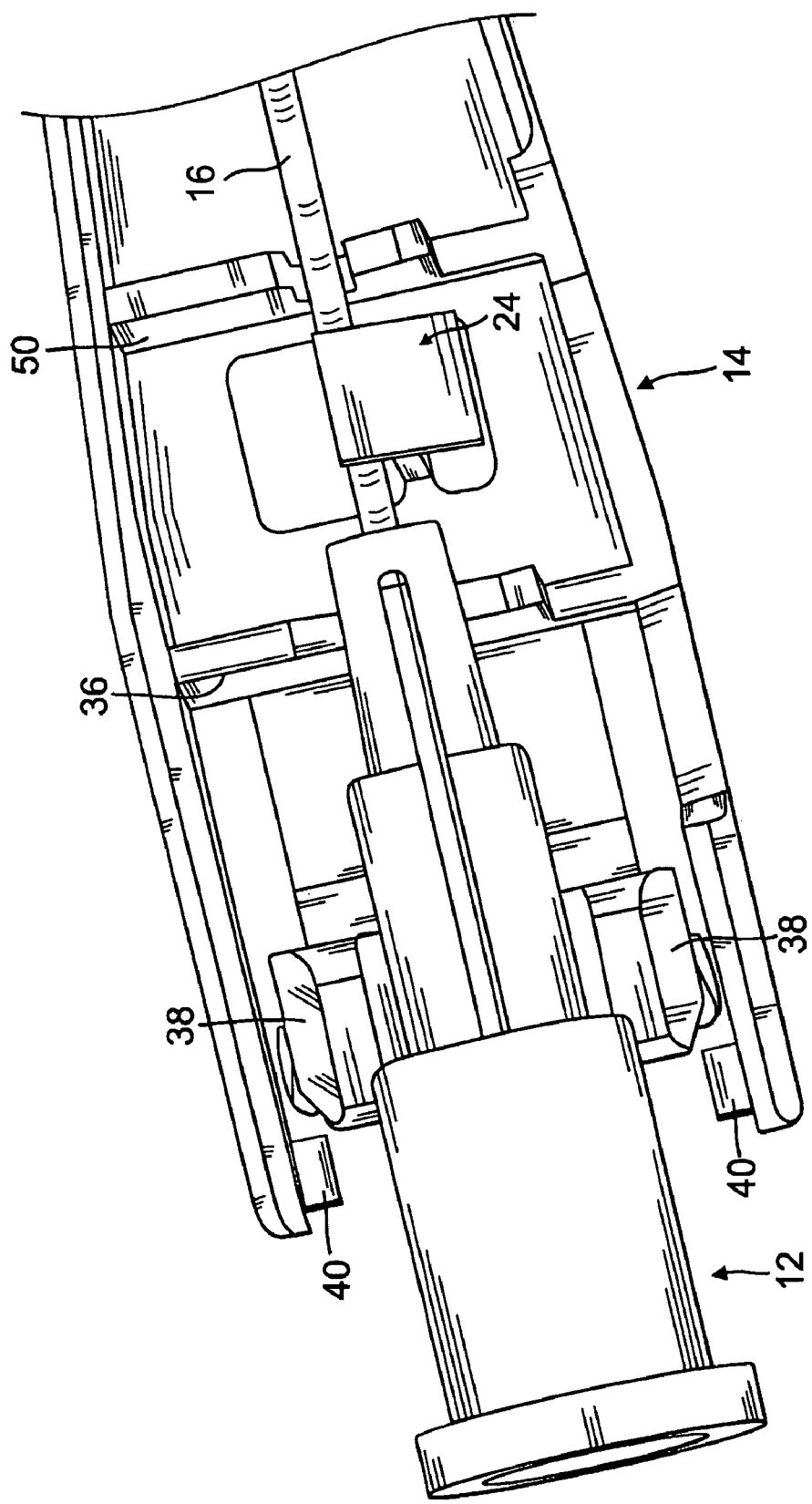
FIG. 3 is a partial perspective view of the hinged cap device of FIG. 2 showing the engagement between the second latching mechanism and the base separated from one another.

The operation of the hinged cap assembly will now be described with reference to FIGS. 2-7. Initially, with reference to FIG. 2, the hinged cap assembly 10 is shown in a packaged or ready position. As the name implies and although not shown, the assembly 10 may be packaged in the configuration shown inside a vacuum pack enclosure having a peelable cover configured for peeling to remove the assembly from the package. In this position, the needle 16 is engaged on the obtuse angle side of the first latching mechanism 24 and extends through the first and second needle alignment members 34, 50. The cap 14 is engaged to the base 12 via abutting surfaces of the tabs 38, 40, that prevent relative rotation between the base and the cap, and the needle holder 17 extends through the hub alignment mechanism 36. To rotate the cap 14 into the open position with respect to the base 12 and expose the needle 16, the tabs 40 on the cap are disengaged from the tabs 38 on the base. In one exemplary embodiment, the tabs 38, 40 may be disengaged by pulling the cap 14 along a longitudinal axis of the needle 16 towards the base such that the surfaces of the tabs 38, 40 become entirely misaligned as shown in FIG. 3. The axial movement of the cap 14 with respect to the base 12 causes the living hinge 18 to curl or distort to accommodate for the axial movement of the cap, resulting in a portion of the cap segment 56 of the living hinge 18 moving proximally of a portion of the base segment 54 (FIG. 4). After a certain amount of axial movement, the stopping edge 19 abuts the walls 36a, 36b of the hub alignment mechanism, thereby limiting the amount of relative axial movement between the base 12 and the cap 14.

As further shown in FIG. 4, the relative angle between the cap 14 and the needle 16 indicates that the cap is rotating radially outwardly to free the needle from the obtuse side of the first latching mechanism 24. As noted above, when the bottom surface of the catch lever 32 engages the needle 16 during the cap rotation to expose the needle, the needle displaces the first latching mechanism 24 and/or the needle deflects to free the needle from the latching mechanism thus allowing the needle. With reference to FIG. 5, the cap 14 has been disengaged from the first latching mechanism 24, and the cap is rotated radially outwardly relative to the needle axis to further expose the needle 16. As shown in FIG. 6, when the cap 14 is further rotated, the wedge 42 on the base engages the gripping plates 44 on the cap to temporarily retain the cap in the open position. In this position, an injection may be performed without the cap 14 interfering with the needle 16. To place the hinged cap device in the secured position, as shown in FIG. 7, the cap is rotated radially inwardly relative to the needle axis such that the needle 16 encounters a top surface 58 of the catch lever 32 and laterally displaces the first latching mechanism 24, or alternatively or in addition thereto the needle deflects to allow the needle to pass around the first latching mechanism. Once the needle 16 is located beneath the acute angle side of the catch lever 32, the needle is secured beneath the catch lever and is prevented from laterally displacing the first latching mechanism 24 and/or from passing around the first latching mechanism regardless of whether the tabs 38/40 are engaged. Additionally, when the needle passes around the catch lever, an audible click and/or a slight vibration may be produced by the interaction of the components, informing a user that the needle has been secured. Although it is not necessary for maintaining the hinged cap device 10 in the secured position, the cap 14 may be moved distally along the needle longitudinal axis to uncurl the living hinge 18 and reengage the tabs 38/40 to provide added security against unwanted rotation.

Another exemplary embodiment of a hinged cap device 110 of the present invention is provided with reference now to FIGS. 8-10b. The hinged cap device 110 comprises a base 112 and a cap 114 (FIG. 9a) having a similar structure to those described above with respect to previous embodiments. The base 112 is connected to the cap 114 by a living hinge. The base 112 further comprises a temporary lock mechanism that, in the present embodiment, is in the form of integral tabs 128 extending from a needle holder 117 adapted to engage a second latching mechanism 126 on the cap 114. The second latching mechanism 126 comprises a pair of latch walls 122 extending perpendicularly from side walls 120a, 120b proximate to a proximal end of the cap 114. The latch walls 122 have a sloped leading edge 135 for directing the temporary lock mechanism in between the gap located between the two walls when the cap is rotated from an open position to a secured position. Additionally, a channel-facing surface 132 of the latch walls 122 includes a notch 124, similar to a barb connector, adapted to engage the tabs 128 on the base 112. A triangular latch support wall 130 extends perpendicularly from the channel-facing surface 132 of each latch wall 122 to delimit over-rotation of the cap when it engages the hub.

Similar to previously described embodiments, the hinged cap device 110 is transformable from a packaged or ready position to an open position and from an open position to a secured position. As shown in FIGS. 9a and 9b, in the ready position, the needle 16 is located on the obtuse angle side of the first latching mechanism 24, and in contact with the projection on one side of its shaft surface, and a top surface of the tabs 128 on the hub or base abuts the notch 124 on each latch wall 122 to prevent relative rotation between the base 112 and the cap 114. To rotate the cap 114 into an open position, the tabs 128 may be disengaged from the notches 124 by holding the hub 112 relatively fixed and moving the cap 114 along a longitudinal axis of the needle 16 towards the base such that the tabs 128 are moved distally of the notches as shown in FIG. 9c to separate the tabs 128 from the notches 124. The axial movement of the cap 114 with respect to the base 112 causes the living hinge 18 to curl or distort to accommodate for the axial movement of the cap. Accordingly, the cap 114 can now be rotated radially away from a longitudinal axis of the needle 16 to expose the needle. In one embodiment, the cap 114 may be squeezed along the two proximal end walls 41a, 41b of the two side walls 120a, 120b to facilitate disengaging the tabs from the latch walls. To place the hinged cap device 110 in the secured position from the open position, the cap 114 is rotated radially back toward the needle axis such that the needles becomes trapped on the acute angle side of the first latch mechanism 24 (FIGS. 10a and 10b). As with previously described embodiments, if desired, the cap 114 can be pulled distally to engage the notches 124 with the tabs 128 for further security against relative rotations between the cap and the base 118.

Figure 11:
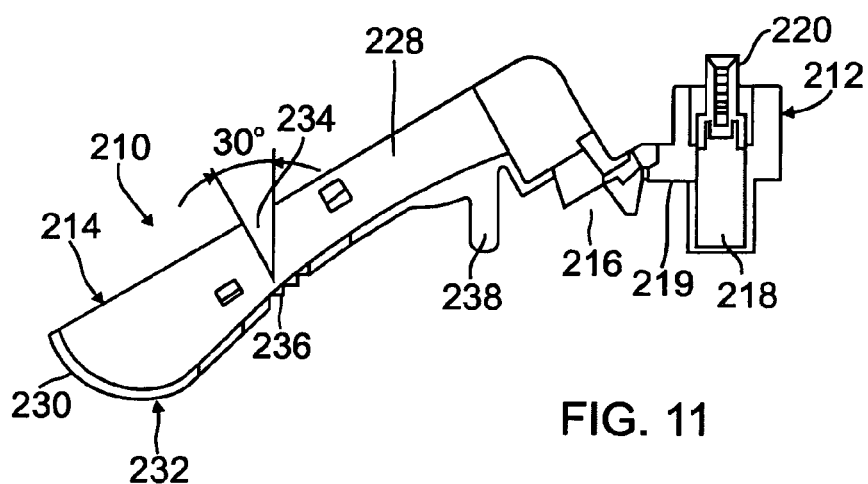
FIGS. 11, 12 and 13 are a side view, a bottom view, and a top view, respectively, of yet another exemplary hinged cap needle device provided in accordance with aspects of the present invention.
Figure 12:
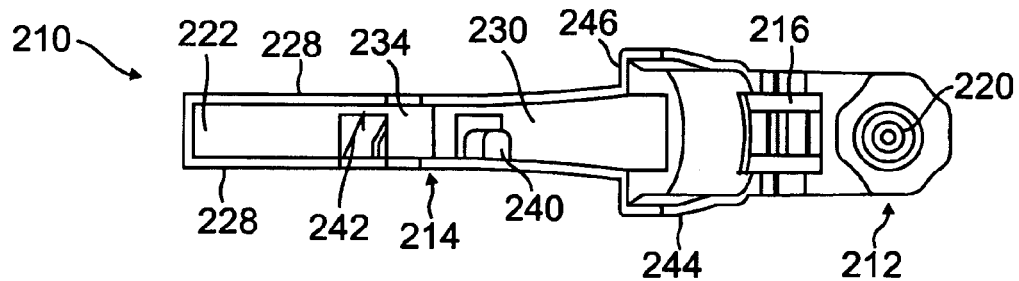
Figure 13:
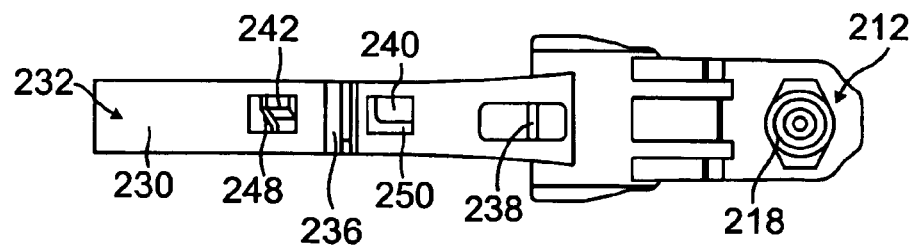

Referring to now FIGS. 11-13, a hinged cap device 210 provided in accordance with aspects of the present invention comprises a hub 212 and a cap 214 connected to one another via a hinge 216. The hub 212 has an open end 218 for coupling to a syringe, a flange 219, and a coupling well 220 for receiving a needle having a sharp needle tip (not shown). The coupling well 220 is configured to grip and couple with the needle without a separate needle hub.

The cap 214 comprises a generally U-shape channel comprising two side walls 228, a base wall 230 and a curved or rounded end 232. A cut-out 234 is incorporated on each side wall 228 thus creating a living hinge 236 at the base wall 230 for pivoting the curved end 232 of the housing over the needle to capture the needle, as further discussed below. In one exemplary embodiment, the cut out has an angle of about 30 degrees, but one of ordinary skill in the art will appreciate that a cut out having an angle of between about 15 degrees to about 45 degrees or greater could also be used to pivot the curved end 232 of the housing over the needle to capture the needle. An integrally formed lever 238 is incorporated for pulling or manipulating the cap 214 to shield the needle or to expose the needle from a semi-lock configuration.

FIG. 12 is a top or plan view of the hinged cap assembly 210 of FIG. 11, looking down at the base wall 230, the coupling well 220, and a channel 222 defined by the two side walls 228. Assuming that a needle is attached to the coupling well 220, the hinged cap assembly 210 is shown in an open or exposed position with the cap 214 pivoted away from the needle to expose the needle tip.

A round detent 240, which resembles a half-cylinder, is molded to one of the side walls 228. A second detent 242 is incorporated near the distal end of the cap, closer to the rounded end 232 and on the other side of the living hinge 236. The second detent 242 resembles a downward leaf spring having one end integrally molded to the same side wall 228 as the round detent and a free end pointed downward into the channel 222. As further discussed below, the round detent 240 is configured to temporarily engage the cap 214 to the needle, such as during transport and prior to use. After use, the second detent 242 in combination with the living hinge 236 is configured to more permanently secure the cap to the needle to prevent needle stick injuries.

Also shown is a wide base section 244 of the cap 214, formed by providing an expanded shoulder 246. The base section 244 is configured to fit around or enwrap the hub 212 when the cap is in a closed or locked position.

FIG. 13 is a bottom or reversed view of FIG. 12. Two viewing windows 248, 250 are incorporated on the base wall 230. The two viewing windows 248, 250 allow a user to verify the locking status of the needle, i.e., to verify whether the needle is trapped behind the semi-lock detent 240 and/or the leaf spring 242.

As briefly mentioned above, following an injection, the cap 214 is configured to more permanently lock to the needle. The second detent 242, in the form of a cantilevered ramp or leaf spring, supported at only one end so that the free end moves or deflects when pushed, is configured to more permanently lock the cap to the needle. The leaf spring 242 has an upper surface or free side and a lower surface or lock side. In a semi-locked configuration, the needle is trapped below the round detent 240 and rests against the free side or upper surface of the leaf spring 242. In the semi-locked configuration, the cap 214 may be pivoted away from the needle by activating the lever 238, which deflects the needle away from the round detent 240.

To more permanently trap the needle within the channel 222 of the cap 214, the cap 214 is first rotated upright over the needle until the needle engages the round detent 240. The curved end 232 of the cap is then pushed so that it pivots about the living hinge 236 (FIG. 11). As the curved end 232 pivots, the base wall 230 and the leaf spring 242 moves in a corresponding radial direction. As the leaf spring 242 moves, the needle is forced under the free end of the leaf spring 242 and is trapped under the lower surface of the leaf spring.

Figure 14:
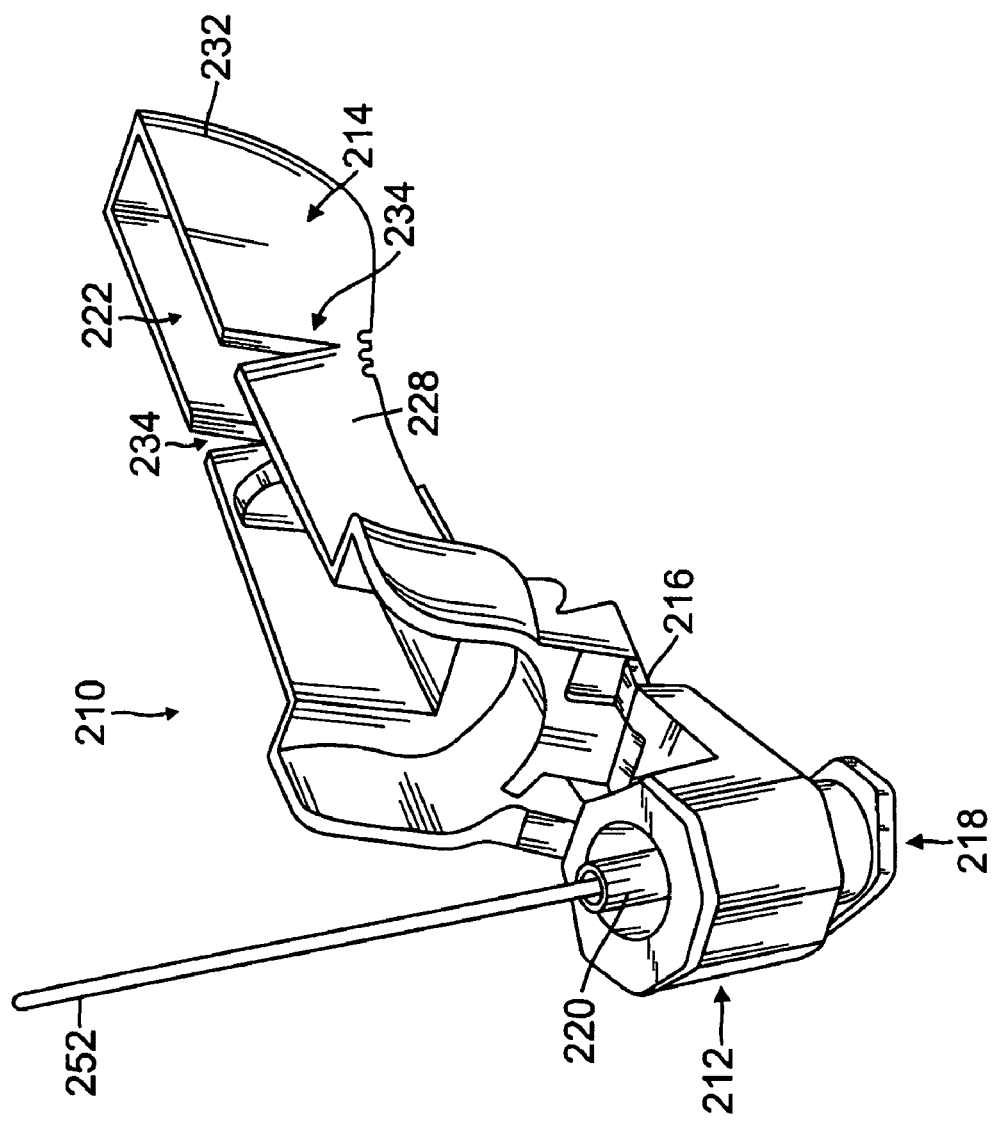
FIG. 14 is a perspective view of the hinged cap device of FIG. 11 shown with a needle attached to the base.

FIG. 14 is a semi-schematic perspective view of the hinged cap assembly 210 of FIGS. 11-13 with the cap 116 in the open position. A needle 252 is shown attached to the coupling well 220, without a separate needle hub.

Figure 15:
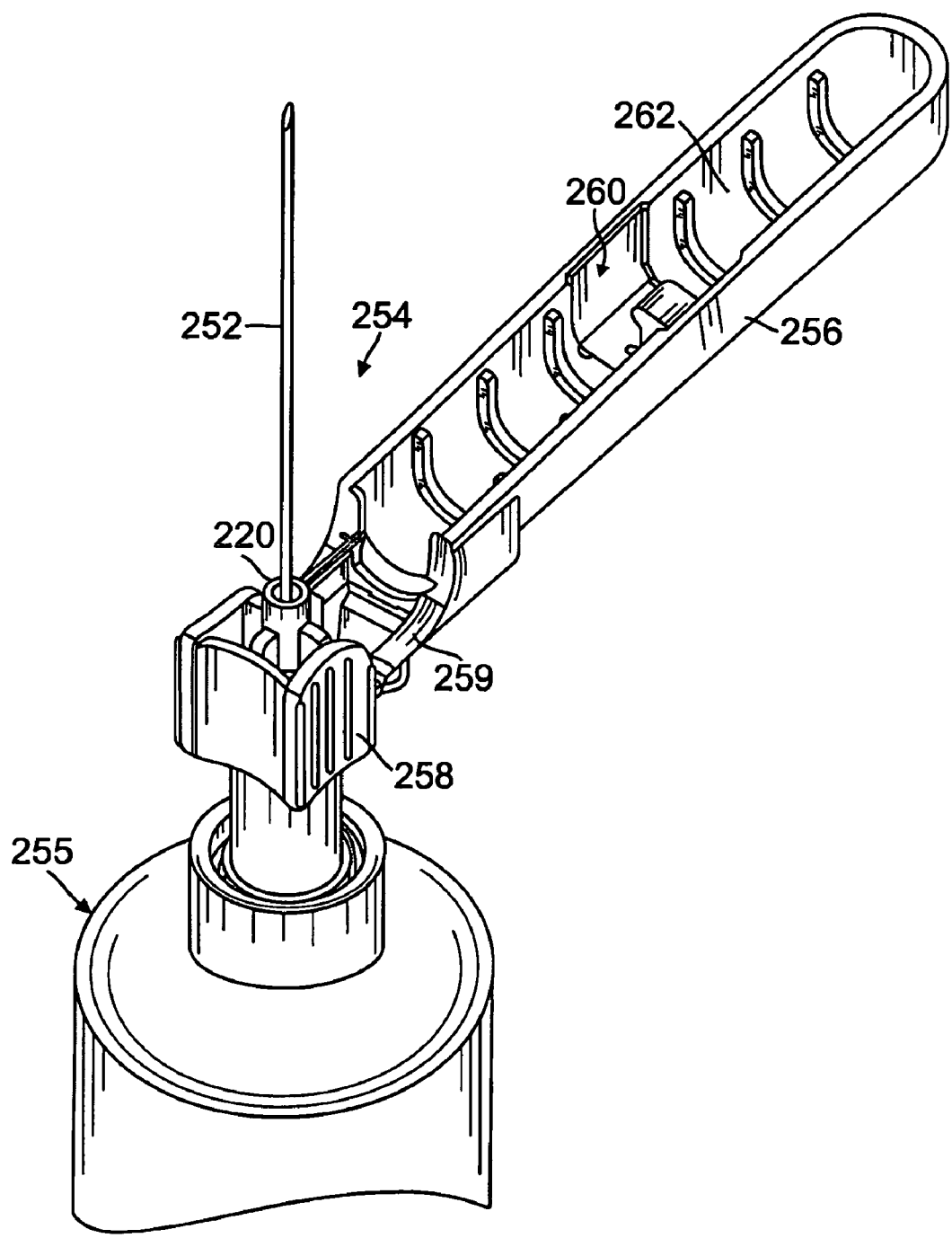
FIG. 15 is a perspective view of still another exemplary hinged cap device provided in accordance with aspects of the present invention, shown mounted on an end of a barrel.

FIG. 15 is a perspective view of yet another exemplary hinged cap device 254 provided in accordance with aspects of the present invention, attached to a syringe 255. The hinged cap device 254 incorporates a cap 256 connected to a needle hub 258 by a living hinge 259. The hinged cap device 254 is moveable between a semi-locked or start position (FIG. 16), in which the cap temporarily covers a needle 252, to an open position wherein the needle is exposed (FIG. 15), from the open position to a capped position (FIG. 17), and from the capped position to a locked position (FIG. 18) in which the needle 252 is permanently trapped within the cap 256. The needle 252 is attached directly to the coupling well 220 of the needle hub 258, although a needle attached to a separate needle hub is contemplated for use with a male luer connector to be located on the hinged cap device 254. In one exemplary embodiment, the cap 256 defines a generally U-shaped channel 262 adapted to house the needle 252. A catch mechanism 260 is incorporated in the channel 262 defined by the cap 256. In one exemplary embodiment, the catch mechanism 260 is made from a metal material and is attached to the cap in a snap lock arrangement, such as detent, dove-tail, or tongue-and-groove lock arrangement. The catch mechanism 260 may also be insert-molded into the cap. The cap 256 is shown in an exposed position, which in one embodiment is about 120 degrees measured from the axis of the needle shaft and an axis defined by the lengthwise direction of the cap.

Figure 16:
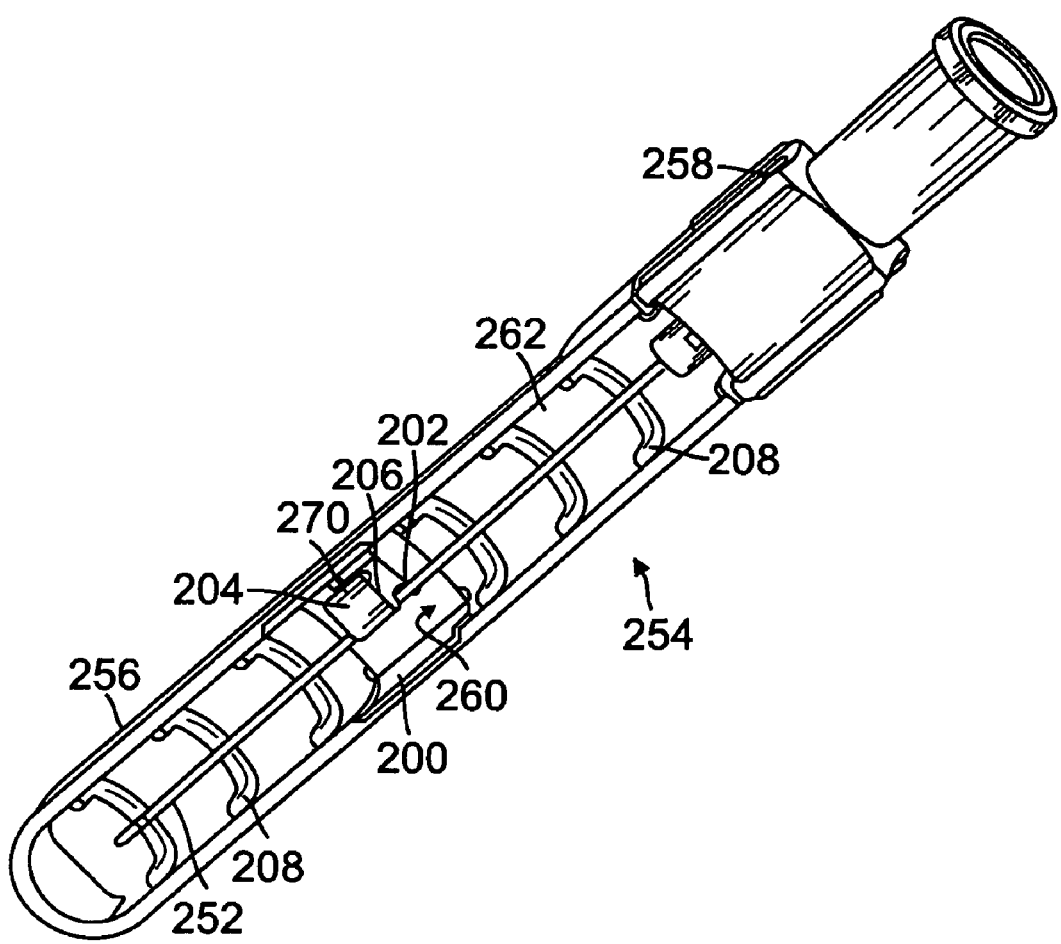
FIG. 16 is a perspective view of the hinged cap device of FIG. 15 in the packaged position for a different viewing angle, shown with the needle rested against an inactive side of the catch mechanism.

FIG. 16 is a perspective view of the hinged cap device 254 of FIG. 15 in the semi-locked or start position, that is also a packaged or shipped position. As shown, the lock mechanism 260 comprises an anchor plate 200, that is similar to a tongue for engaging a groove located on the cap. A cantilevered member 202 extends from the anchor plate 200, or to another section that extends from the anchor plate, and comprises an arcuate joint 203 and a hook arm 270, (more clearly shown on FIG. 19) that comprises an inactive surface 204 and an active surface 206, located on the hook arm facing in the opposite direction from the inactive surface 204. A plurality of ribs 208 are optionally incorporated in the cap for enhancing the structural rigidity of the cap.

In the start position shown in FIG. 16, the needle 252 is positioned in a temporary locked position against the catch mechanism 260, in which the needle is held temporarily against the arcuate joint 203. To use the needle, the cap 256 is pivoted radially outwardly to expose the needle, which deflects the needle 252 and/or the catch mechanism 260 to free the needle from the catch mechanism. The cap 256 is pivoted until it is in the open position shown in FIG. 15. The needle is now ready for use.

Figure 17:
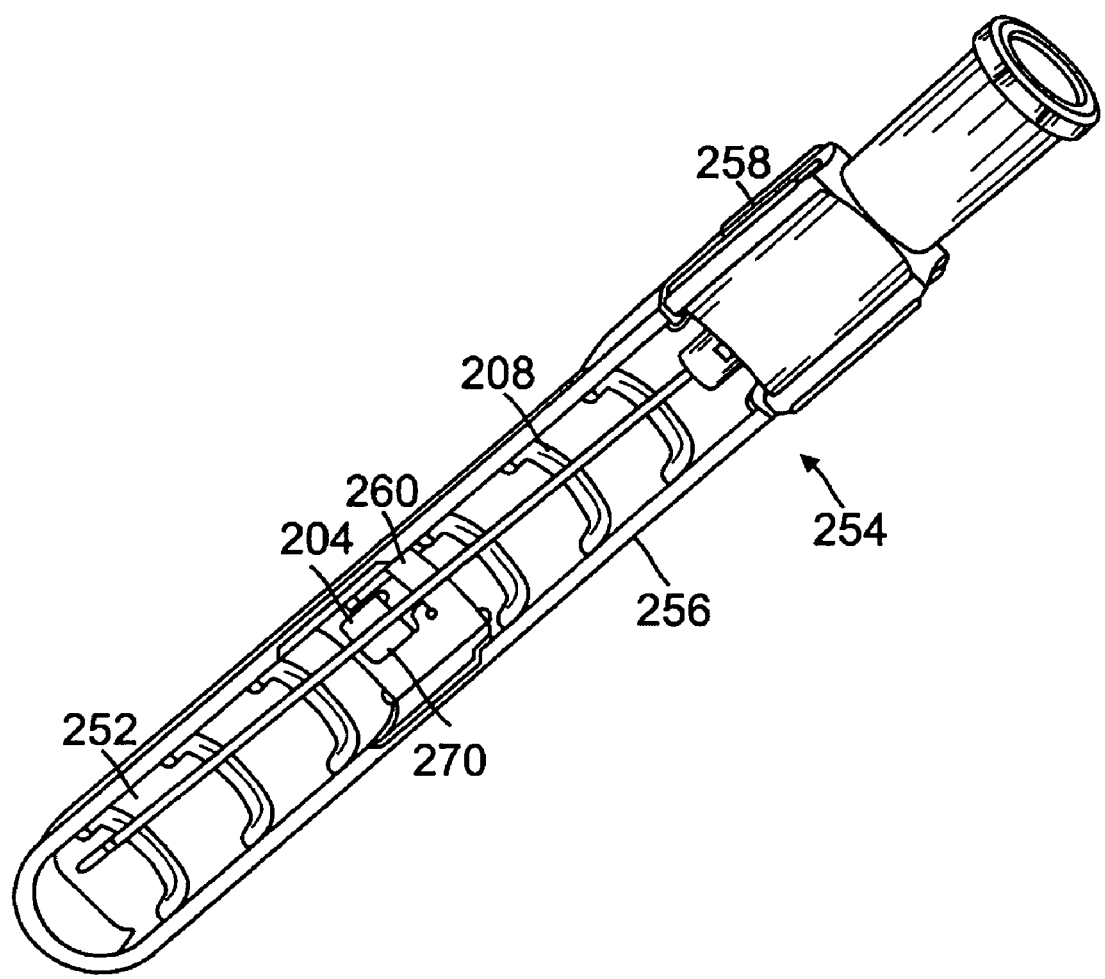
FIG. 17 is a perspective view of the hinged cap device of FIG. 16 shown with the needle pushed against the catch mechanism, immediately prior to latching or locking.

FIG. 17 is a perspective view of the hinged cap device 254 with the needle 252 pushed against the inactive surface 204 of the hook arm 270. Once fluids are drawn into the syringe 255 (FIG. 15) for performing an injection, the cap 214 may be pivoted back in alignment over the needle 252 by pushing the cap, using either a finger to push the cap or pushing the cap against a surface. Care should be taken at this time not to fully lock the needle before administering the injection. To perform an injection, the user again pivots the cap 256 away from the needle (FIG. 15) to the open position, administers the injection, and recaps the needle to the position shown in FIG. 17.

Figure 18:
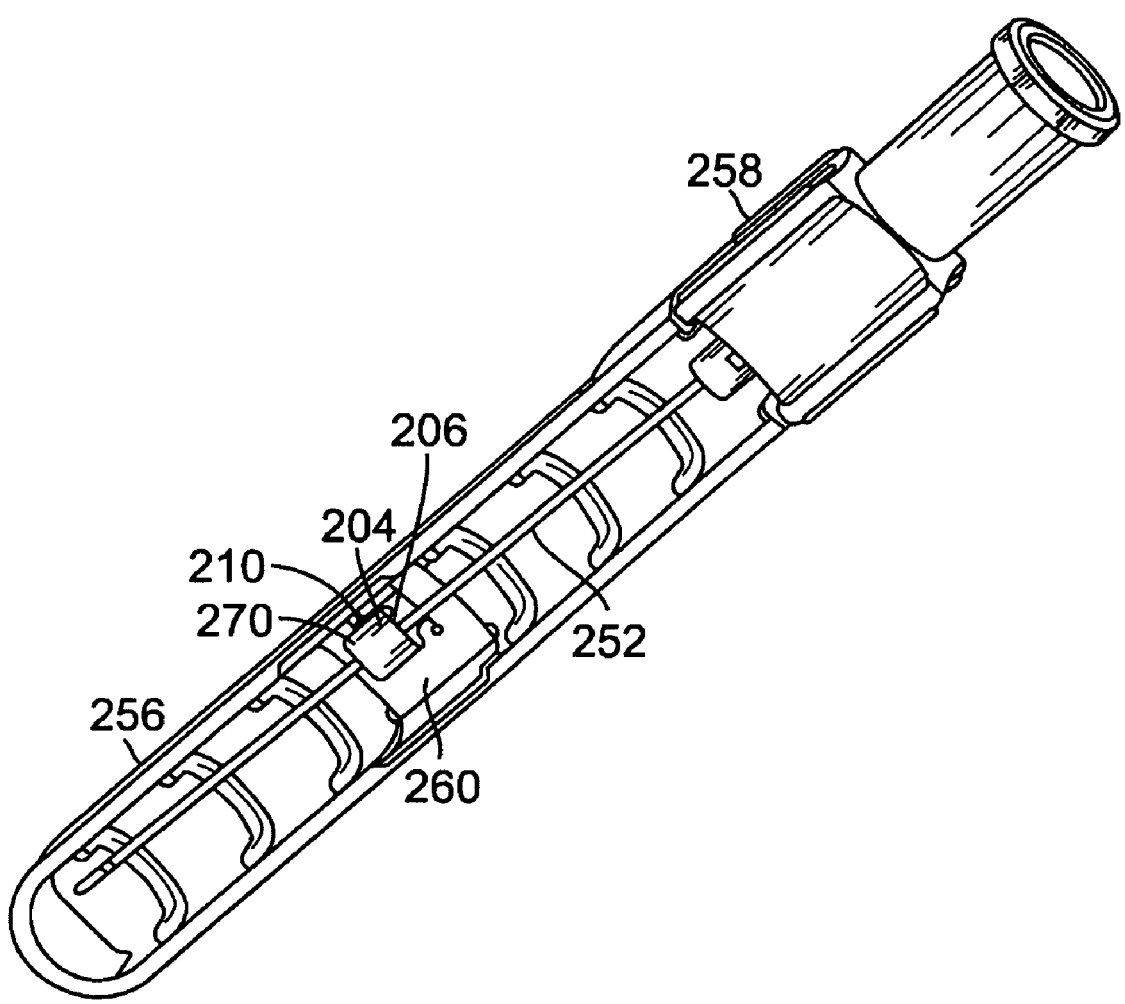
FIG. 18 is a perspective view of the hinged cap device of FIG. 17 shown with the needle in a locked position.

FIG. 18 is a perspective view of the needle 252 moved to a secured position. As shown, the needle 252 is moved to the active surface 206 of the hook arm 270. In one exemplary embodiment, this is accomplished by pushing the cap 256 further upright so that the needle 252 is moved further into the channel 262 defined by the cap. This further movement on the cap causes the needle 252 to deflect, the hook arm 270 to deflect, or both. As is readily apparent to a person of ordinary skill in the art, the hook arm 270 is angled so that the plane defined by the inactive surface 204 (FIG. 17) is angled or sloped relative to the plane defined by the motion of the cap. This orientation allows the needle, the hook arm, or both to deflect when the cap is pivoted. The cap is pivoted until the needle 252 is moved past the end or ledge 264 of the hook arm 270, at which time the needle recoils or recovers and moves under the hook arm against the active surface 206.

Figure 19:
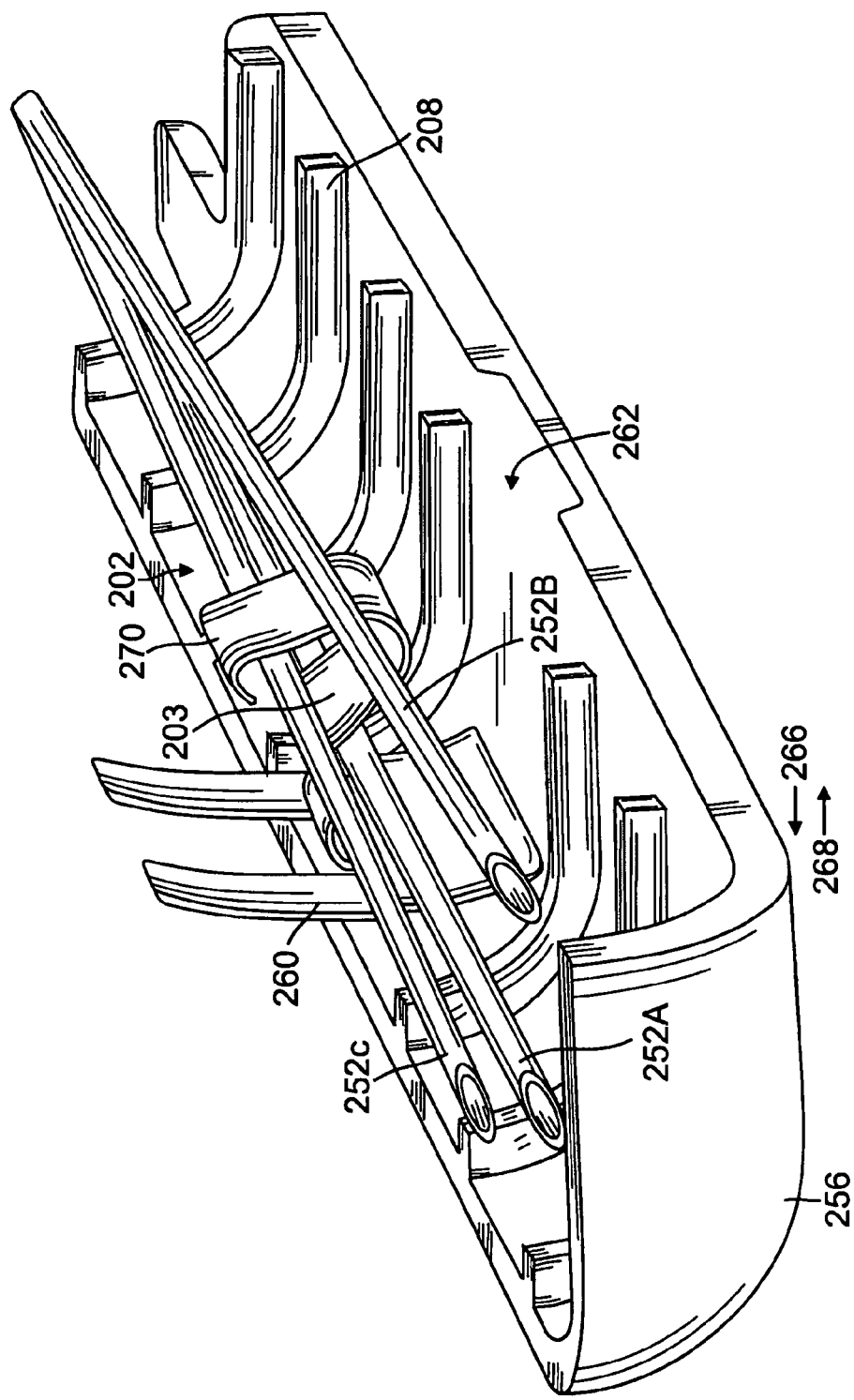
FIG. 19 is a schematic view of the hinged cap device of FIG. 15 showing the three needle positions depicted in FIGS. 16-18.

FIG. 19 is a partial perspective view of the hinged cap device 254 of FIG. 15 with the needle 252 shown in three different positions: (1) a start position, (2) a capped but not secured position, and (3) a secured position. In the start position, the needle 252 is positioned in a temporary locked position, indicated at 252A, against the arcuate joint 203 of the cantilevered member 202. To use the needle, the cap 256 is pivoted outwardly in the direction of the open arrow 266, which deflects the needle free from the catch mechanism. After use, the cap 256 is pivoted in the direction of the closed arrow 268 until the needle 252 contacts the hook arm 270 of the catch mechanism, indicated at 252B. Further advancing the cap in the closed arrow 268 direction will cause the needle to deflect due to the hook arm 270, the hook arm to deflect due to the needle, or both. As the needle moves across the tip or end 264 of the hook arm 270, the needle is trapped on the active side 206 of the hook arm, indicated at 252C.

Figure 20:
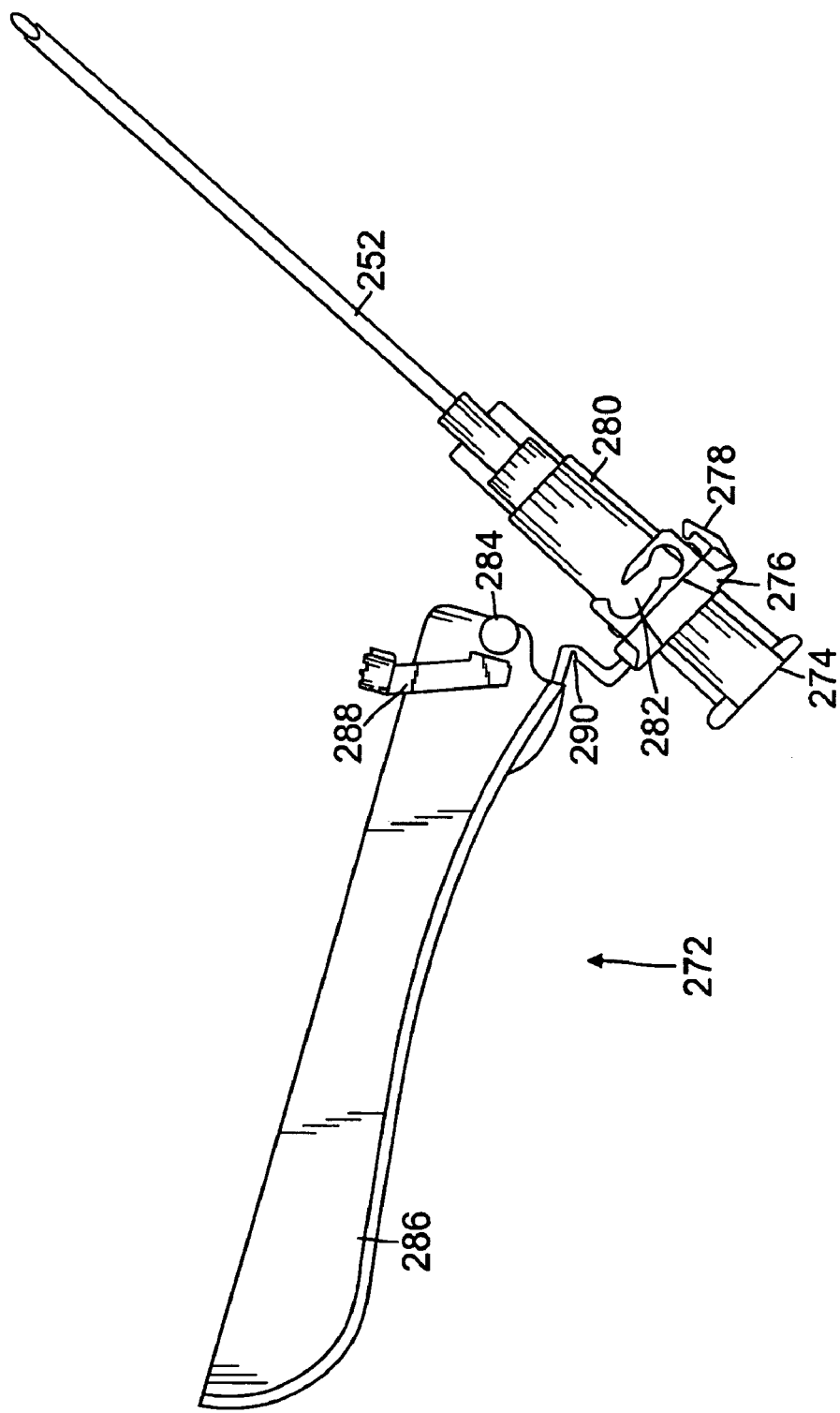
FIG. 20 is a side view of yet another exemplary embodiment of a hinged cap device provided in accordance with aspects of the present invention.

With reference now to FIG. 20, another exemplary embodiment of a hinged cap device 272 mountable on a syringe is shown. The hinged cap device 272 may include any of the latching mechanisms described above, among others, and is shown with the cap pivoted away from a needle 252, in an exposed or open position. The hub 274 incorporates a flange 276, including a lock lever 278 for locking a needle hub 280 having the 252 needle attached thereto and a socket 282 for receiving a boss 284 on the cap 286. The cap 286 further includes a gripping lever 288 for pushing or pulling on the cap to engage the boss 284 to the socket 282. In one exemplary embodiment, the hinged cap device includes two sockets 282, two bosses 284, and two gripping levers 288 located on opposite sides of the needle hub 274 and the cap 286.

Figure 21:
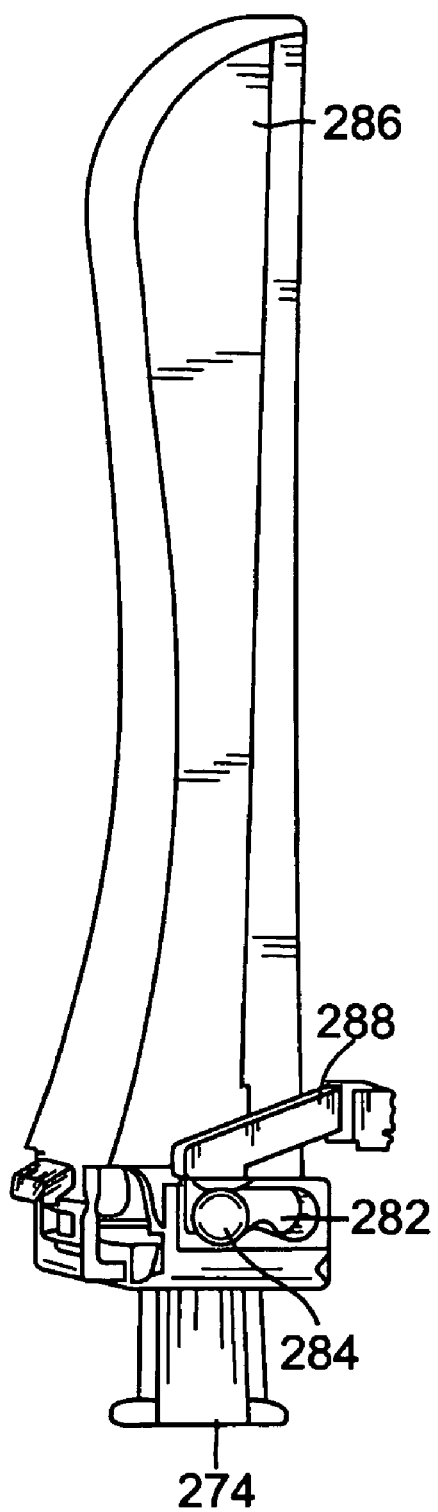
FIG. 21 is a side view of the hinged cap device of FIG. 20 in a semi-locked position.

As shown in FIG. 21, the cap 286 may be rotated from the open position to a semi-locked position in which the cap 286 is aligned over the needle and the boss 284 is engaged in a first groove of the socket 282. In the semi-locked position, the cap can be pivoted away from the needle to an open position or the gripping lever 288 may be pulled or pushed to move the boss to the second groove of the socket 282 to a locking position. The hinge 290 is an articulating hinge, capable of both pivoting and translating to move the boss to a fully locked position.

Figure 22:
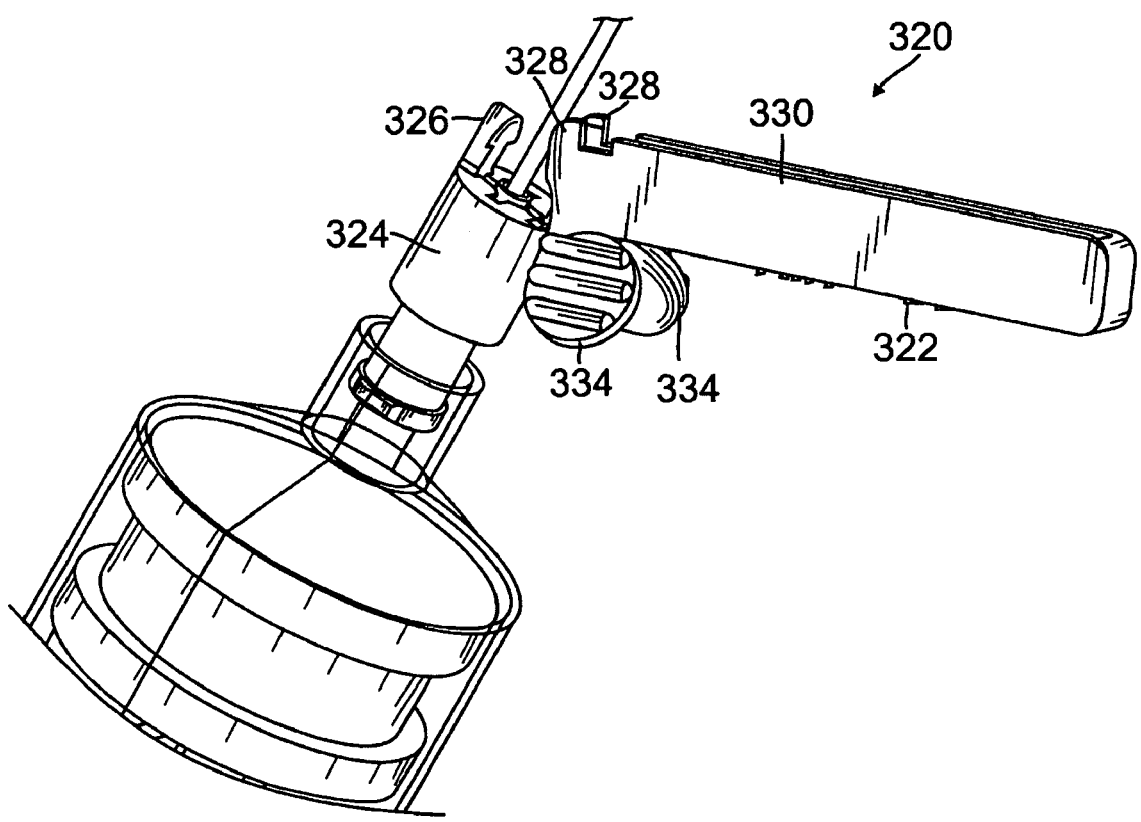
FIG. 22 is a perspective view of still another exemplary embodiment of a hinged cap device provided in accordance with aspects of the present invention.

In another exemplary embodiment of a hinged needle device 320 as shown in FIG. 22, provided in accordance with aspects of the present invention mountable on a syringe. Similar to other hinged cap device embodiments described herein, the hinged cap device 320 incorporates a cap 322 and a hub 324 for capturing and shielding a needle to prevent inadvertent needle stick. The hub 324 incorporates a post 326 and a pair of catch arms 328 for grabbing or engaging the post 326. The catch arms 328 extend from the two side walls 330 of the cap. A pair of lever arms 334 also extend from the two side walls 330, but in a direction opposite from the two catch arms 328. When the two catch arms 328 are squeezed together, or towards one another, they deflect the two side walls, which then causes the two catch arms to move farther apart from one another.

Figure 23:
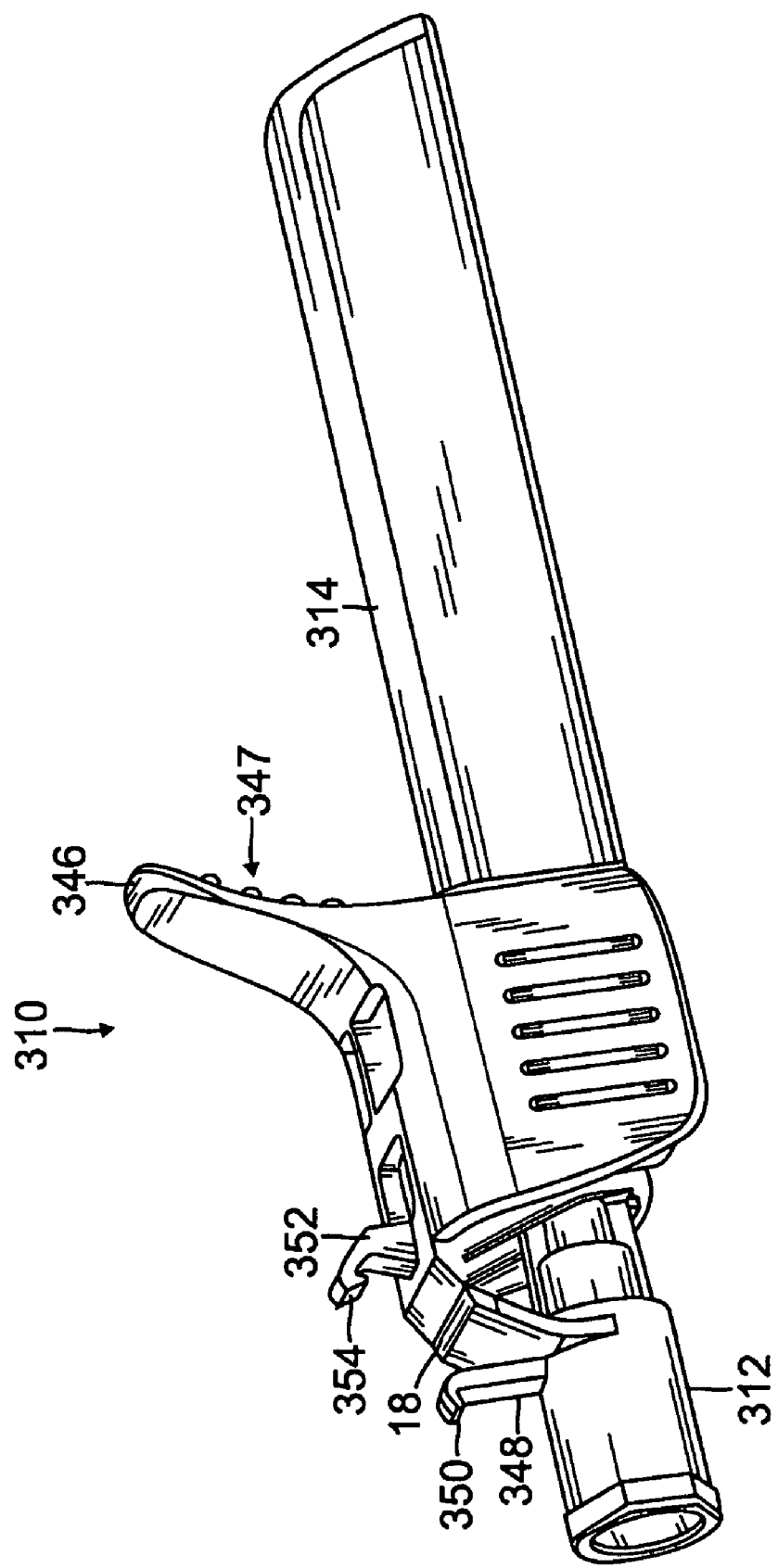
FIG. 23 is a perspective view of yet another exemplary embodiment of a hinged cap device provided in accordance with aspects of the present invention.

Yet another exemplary embodiment of a hinged cap device 310 of the present invention is shown in FIGS. 23-27. With reference now to FIG. 23, the hinged cap device comprises a base 312 connected to a cap 314 by a living hinge 18, the living hinge being biased toward an initial packaged or ready position. Similarly to previously described embodiments, the cap can be rotated from the ready position to an open position (FIG. 24), in which a needle 316 is exposed and from the open position to a secured position in which the needle 316 is secured within the cap by the first latching mechanism 24. A push tab 346 is provided to aid in rotation of the cap 314 between various positions, the push tab including a gripping surface 347, for example, a plurality of raised protrusions or bumps, to provide a user with a more secure hold on the cap. The push tab 346 may also be contoured to generally conform to a user's finger, thereby providing a comfortable feel for the user. Additionally, the base 312 includes a base engagement prong 348 having a detent or hook 350 at an end adapted to engage a detent or hook 354 on a cap engagement prong 352 to temporarily lock the cap 314 in the open position, as described in more detail below.

Figure 24:
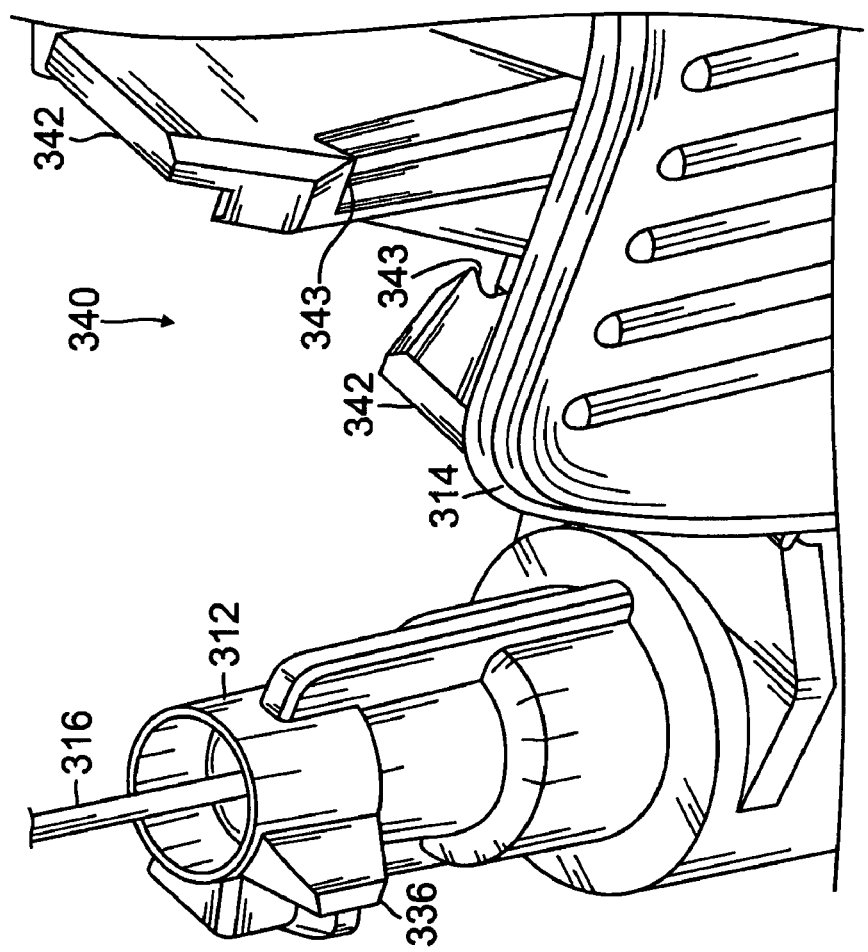
FIG. 24 is a detail view of a base and a second latching mechanism of the hinged cap device of FIG. 23.
Figure 25:
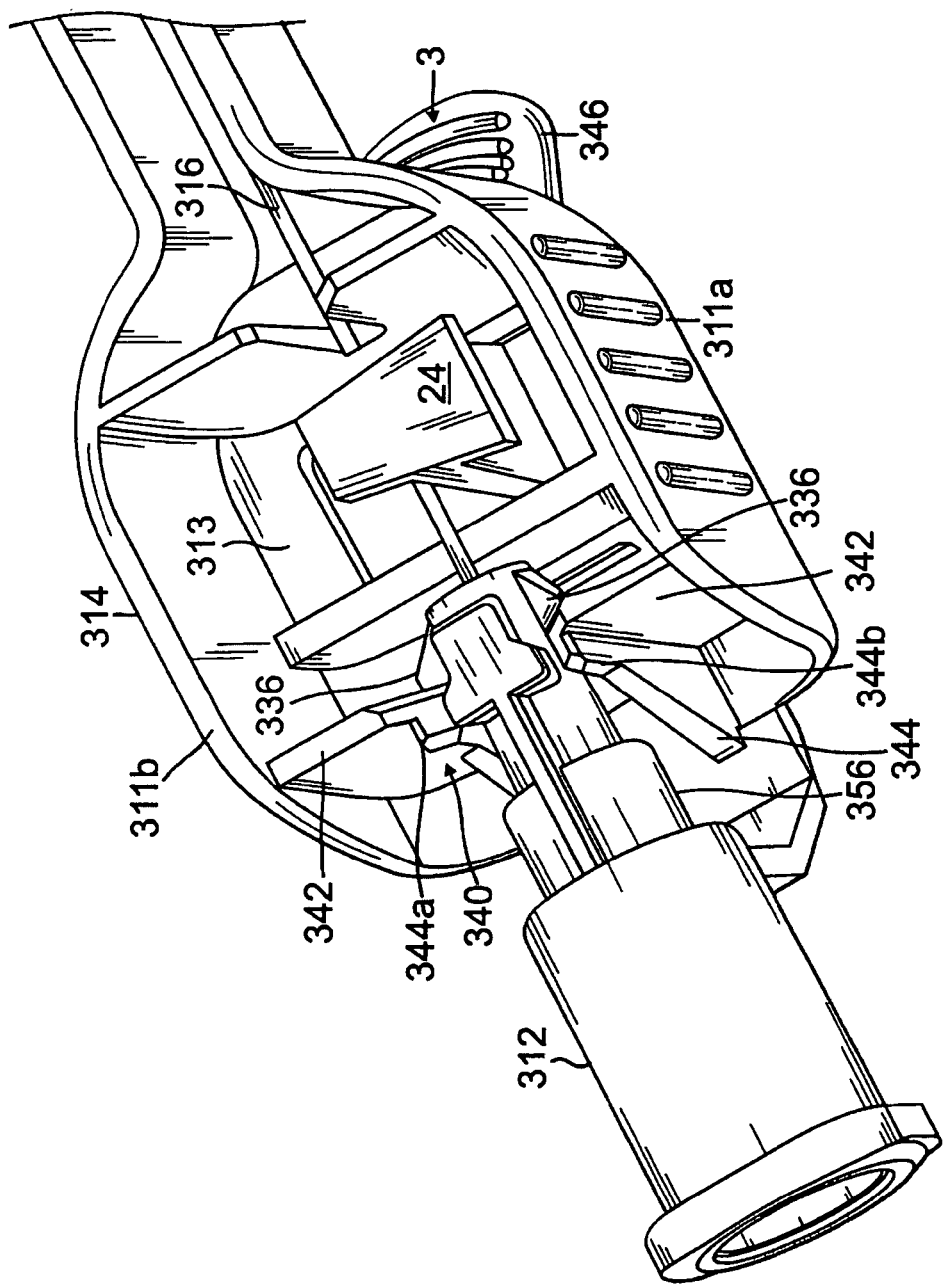
FIG. 25 is a partial perspective view of the hinged cap device of FIG. 23 showing the engagement between the second latching mechanism and the base.

With reference now to FIGS. 24 and 25, the cap 314 includes two side walls 311a, 311b, defining an open channel 313 therebetween. The cap 314 further includes a second latching mechanism 340, including two latch walls 342, each latch wall extending orthogonally from one side wall 311a, 311b and including an undercut or notch 343 adapted to receive a respective tab 336 on the base 312, similarly to the embodiment described with respect to FIGS. 8-10b. In one exemplary embodiment, the notches 343 form an acute angle with the latch wall 342 to provide additional security against rotation for the base 312 when the tabs 336 are engaged with the notches. Additionally, a latch support wall 344 extends perpendicularly from each latch wall 342 and having tapered or angled edges below generally constant upper edges for structurally supporting the latch wall 342. The upper generally constant edges 344a, 344b are configured to abut the base to delimit axial movement of the base relative to the cap, as further discussed below.

Figure 27:
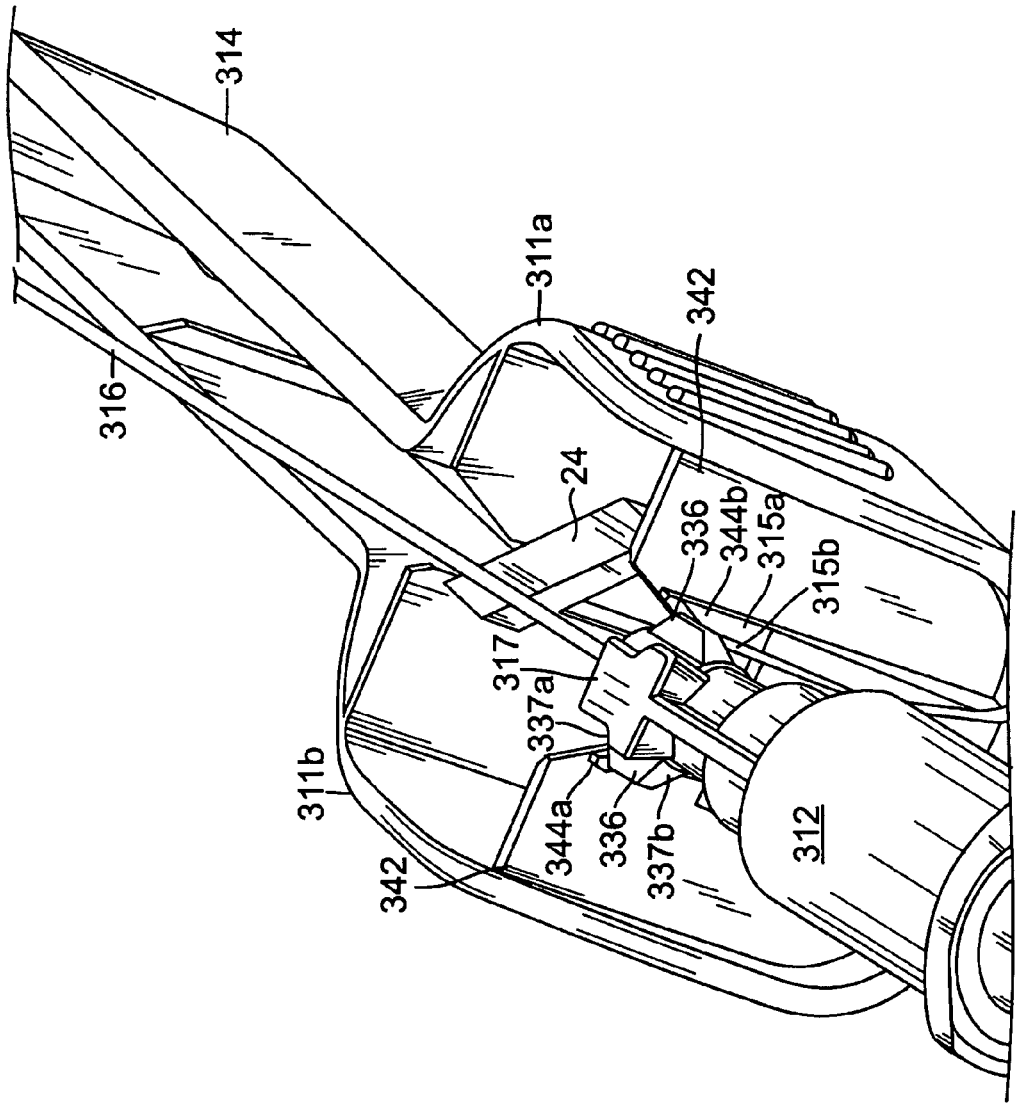
FIG. 27 is a perspective view of the hinged cap device of FIG. 23 between an open position and a secured position.

With reference now also to FIG. 27, the tabs 336 extending from the base 312 have angled leading and trailing edges 337a, 337b that generally form an obtuse angle with a surface of the base that they contact and allow for easier disengagement from and engagement to the cap during rotation. Additionally, upper and lower surfaces 315a, 315b of the tabs 336 are generally sloped upward toward a reinforcement member 317 of the base 312 to substantially match an angle of the notch 343 such that the tabs generally form a V-shape with the base in cross-section. Additionally, the sloped lower surface 315b on the two tabs 336 provide less resistance between the latch walls 342 and the tabs 336 when the cap is rotated from the open position to the secured position, allowing easier rotation of the cap into the secured position. As will be appreciated by one of ordinary skill in the art, tabs and corresponding notches of varying shapes, sizes, and configurations may be used without departing from the spirit and scope of the invention.

Figure 26:
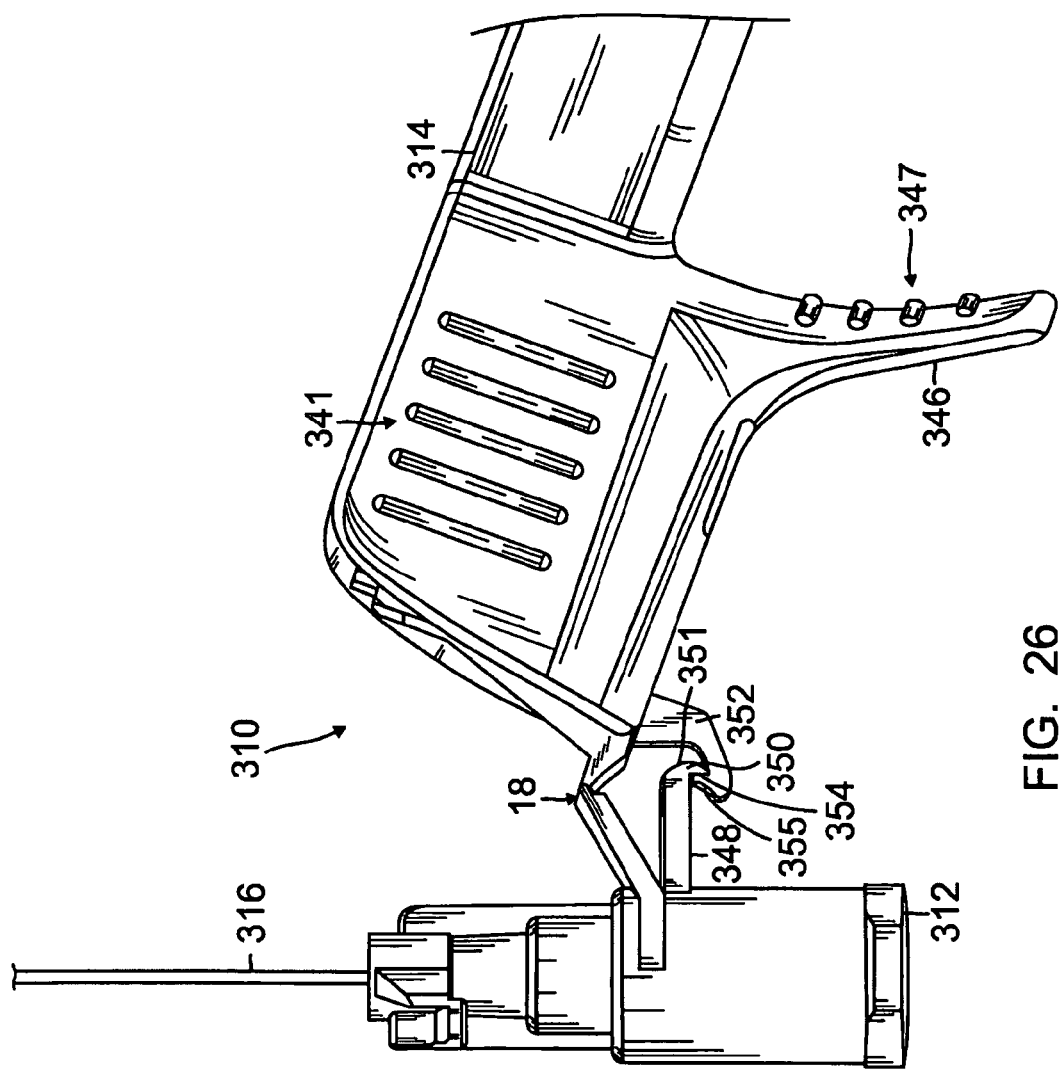
FIG. 26 is a perspective end view of the hinged cap device of FIG. 23 showing the cap rotated away from the needle to expose the needle and the cap temporarily locked to the base.

With reference now to FIG. 26, the hinged cap device 310 is shown in the open position wherein the cap 314 has been rotated such that the hook 354 on the cap engagement prong 352 is engaged with the hook 350 on the base engagement prong 348. As the cap 314 is rotated radially, a contact surface 355 of the cap engagement prong contacts a contact surface 351 of the base engagement prong 348 and, if enough force is applied on the cap 314 toward the base 312, the engagement prongs 348, 352 deflect and snap into the temporary locked arrangement as shown. When the engagement prongs 348, 352 are snapped together, the components may produce a sound or a vibration to indicate their engagement to a user. In one exemplary embodiment, the contact surfaces 351, 355 are arcuate to require less resistance to snap the engagement prongs 348, 352 together. To disengage the engagement prongs 348, 352, a radial force may be applied to the cap 314 sufficient to deflect the engagement prongs and to allow the hooks 350, 354 to separate. As one of ordinary skill in the art will appreciate, the length of the hooks 350, 354 and the widths of the engagement prongs 348, 352 may be varied based on the amount of force desired to disengage the engagement prongs.

To place the hinged cap device 310 onto a syringe (not shown), the user may grasp the cap 314 at a contoured gripping surface 341 location of the side walls 311a, 311b, thereby slightly compressing and deforming the cap and causing the latch walls 42 to exert a radial pressure on the tabs 336. As such, a user can restrict relative axial movement between the base 312 and the cap 314 when the hinged cap device 310 is mounted onto a syringe. However, one of ordinary skill in the art will appreciate that a hinged cap device having a rigid cap could still be suitable and mountable onto a syringe. Similarly to previously described embodiments, to move the cap 314 from the ready position (FIG. 25) to the open position (FIG. 26), the cap is moved axially toward the base 312 to disengage the tabs 336 from the second latching mechanism 340. The relative axial movement between the base 312 and the cap 314 is limited by the stopping edge 356 abutting the latch support walls 344, and more particularly the upper generally constant edges 344a, 344b. Either the base is held stationary and the cap is axially moved or vice versa or both. Once the tabs 336 have been disengaged, the cap 314 may be rotated radially outwardly away from the needle 316 to expose the needle. After use, the cap 314 may be rotated radially inwardly toward the needle 316 where the first latching mechanism 24 will engage the needle and secure it under the acute angle side, as described above. In one embodiment, the living hinge is configured with a self bias by sizing the tabs on either side of the living hinge with sufficient material and resiliency so that the it tends to push the base and the cap axially away from one another toward the ready position to uncoil to its more relaxed position. As such, when the cap is moved to a locked position, the tabs 336 will reengage the notches 343 of the latch walls 342 by the bias action of the living hinge. However, as noted above, such reengagement is not necessary to secure the needle 316 within the cap 314. Additionally, one of ordinary skill in the art will appreciate that the living hinge does not need to be biased into the ready position.

Although limited hinged cap embodiments and their components have been specifically described and illustrated, many modifications, combinations, and variations of the embodiments will be apparent to those skilled in the art. For example, the length, size, colors, and other appearances of the hub may be modified, and the needle may be attached directly to the hub on the hinged cap or as a separate hub attached via a luer fitting. Furthermore, it is understood and contemplated that features specifically discussed for one hinged cap embodiment may be adopted for inclusion with another hinged cap embodiment provided the functions are compatible. For example, the cap living hinge of FIGS. 11-14 may be incorporated into the caps of the various other embodiments. Accordingly, it is to be understood that the hinged cap devices and their components constructed according to principles of this invention may be embodied other than as specifically described herein. The invention is also defined in the following claims.

What is claimed is:

1. A hinged cap device for use with a syringe comprising:
a base defining an interior cavity for mounting onto a tip;
a cap comprising a base wall, a first side wall, and a second side wall defining an open channel, wherein the cap is connected to the base by a living hinge, and wherein the cap is moveable from a ready position to an open position to expose a needle having a needle shaft and a needle tip, and from the open position to a secured position to prevent relative rotation between the cap and the base;
a first latching mechanism on the cap for engaging the needle, the first latching mechanism locatable on a first side of the needle shaft in the ready position and locatable on a second side of the needle shaft in the secured position; wherein the needle is disengageable from the first latching mechanism in the ready position, and wherein the needle is not disengageable from the first latching mechanism in the secured position; and
a second latching mechanism on the cap for engaging the base to prevent relative rotation between the cap and the base when the cap is in the ready position, wherein the second latching mechanism comprises two spaced apart tabs extending in a proximal direction away from the needle tip; wherein each tab of the two spaced apart tabs is adapted to abut a respective base tab located on the base; and wherein the two spaced apart tabs are separable from the two respective base tabs on the base by moving the cap axially along a lengthwise axis of the needle relative to the base.

2. The hinged cap device of claim 1, wherein the first latching mechanism further comprises a projection attached to the cap and extending into the open channel; and a catch lever straddling the projection to form an obtuse angle side and an acute angle side.

3. The hinged cap device of claim 2, wherein the needle is on the obtuse angle side in the ready position and on the acute angle side in the secured position.

4. The hinged cap device of claim 1, wherein the first latching mechanism is laterally deflectable with respect to a longitudinal axis of the needle.

5. The hinged cap device of claim 1, wherein the base tabs are located on a second cylinder section of the base, which is smaller in outside diameter than a first diameter section of the base.

6. The hinged cap device of claim 1, wherein the living hinge is distortable to allow the second latching mechanism to be disengaged from the base tabs.

7. The hinged cap device of claim 1, wherein the base further comprises a wedge and the cap further comprises a pair of spaced apart gripping plates defining a gripping cavity therebetween, the wedge adapted to move into the gripping cavity to engage the gripping plates to temporarily maintain the cap in the open position.

8. The hinged cap device of claim 1 comprising a single integral device.

9. The hinged cap device of claim 8, wherein the device is injection molded.

10. The hinged cap device of claim 1, wherein the first side wall comprises a notch having two end wall edges defining an angle therebetween.

11. The hinged cap device of claim 10, further comprising a living hinge on the cap spaced from the living hinge located between the cap and the base.

12. A hinged cap device for use with a syringe comprising:
a base defining a cavity to receive a syringe for mounting onto a tip of the syringe;

a cap comprising a base wall, a first side wall, and a second side wall defining an open channel, the cap connected to the base by a living hinge and rotatable between a ready position and a secured position;

a first latching mechanism on the cap for engaging a needle to prevent relative rotation between the cap and the base when the cap is in the secured position; and a second latching mechanism comprising at least one base tab protruding from the base and engaging at least one tab on the cap, wherein the at least one base tab is disengageable from the at least one tab by axially moving the cap along a lengthwise axis of the needle relative to the base.

13. The hinged cap device of claim 12, wherein the first latching mechanism further comprises a projection attached to the cap and extending into the open channel, and a catch lever straddling the projection to form an obtuse angle side and an acute angle side.

14. The hinged cap device of claim 13, wherein the needle is on the obtuse angle side in the ready position, and wherein the needle is on the acute angle side in the secured position.

15. The hinged cap device of claim 12, wherein the first latching mechanism is laterally deflectable with respect to a longitudinal axis of the needle.

16. The hinged cap device of claim 12, wherein the second latching mechanism comprises a pair of latch walls, one latch wall each extending from both the first side wall and the second side wall, and wherein each latch wall comprises a notch adapted to engage a respective tab on the base.

17. The hinged cap device of claim 12, wherein the second latching mechanism comprises a pair of cap tabs, one cap tab extending from both the first side wall and the second side wall, and wherein each cap tab is adapted to abut a respective tab on the base.

18. The hinged cap device of claim 12, wherein the living hinge is distortable to allow the second latching mechanism to be disengaged from the base.

19. The hinged cap device of claim 12, the base further comprising a wedge and the cap further comprising a pair of gripping plates, the wedge adapted to engage the gripping plates to temporarily maintain the cap in an open position in which the needle is exposed.

20. A method for operating a hinged cap device, the hinged cap device comprising a base for supporting a needle, a cap connected to the base by a living hinge, a needle latching mechanism on the cap for engaging the base, the method comprising:

moving a cap axially along a lengthwise direction of a needle to distort the living hinge;

rotating the cap radially outwardly relative to the needle to expose the needle;

engaging the cap to the base in the cap open position; and wherein the needle latching mechanism comprises a base tab protruding from the base and engaging at least one tab on the cap, wherein the base tab is disengageable from the at least one tab by axially moving the cap along a lengthwise axis of the needle relative to the base.

21. The method of claim 20, further comprising a second latching mechanism on the cap for engaging the needle, the method further comprising rotating the cap radially inwardly relative to the needle to shield the needle and to engage the base tab to the at least one tab on the cap.

22. The method of claim 21, the second latching mechanism comprising an obtuse angle side and an acute angle side; wherein before rotating the cap radially outwardly, the needle is on the obtuse angle side; and wherein after rotating the cap radially inwardly, the needle is on the acute angle side.

* * * * *